[12] United States Patent
Liau et al.

(10) Patent No.: US 6,610,534 B2
(45) Date of Patent: Aug. 26, 2003

(54) INDUCTION OF BLOOD VESSEL FORMATION THROUGH ADMINISTRATION OF POLYNUCLEOTIDES ENCODING SPHINGOSINE KINASES

(75) Inventors: Gene Liau, Darnestown, MD (US); Steingrimur Stefansson, Gaithersburg, MD (US); Joseph Su, Germantown, MD (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/970,516

(22) Filed: Oct. 4, 2001

(65) Prior Publication Data

US 2002/0099029 A1 Jul. 25, 2002

Related U.S. Application Data

(60) Provisional application No. 60/238,230, filed on Oct. 5, 2000.

(51) Int. Cl.[7] .................. C12N 15/63; A01N 43/04; A61K 31/70; C07H 21/04
(52) U.S. Cl. .................. 435/320.1; 435/252.3; 514/44; 536/23.1; 536/23.5; 536/23.4
(58) Field of Search .................. 435/320.1, 325, 435/252.3; 514/44; 536/23.1

(56) References Cited

U.S. PATENT DOCUMENTS 5,932,540 A * 8/1999 Hu et al. .................. 514/2

FOREIGN PATENT DOCUMENTS

| WO | WO 99/61581 | 12/1999 |
|---|---|---|
| WO | WO 00/70028 | 11/2000 |

OTHER PUBLICATIONS

Boguslawski, et al., "Sphingosylphosphorylcholine Induces Endothelial Cell Migration and Morphogenesis," *Biochemical and Biophysical Research Communications*, 272:603–609 (Jun. 7, 2000).
Hla, et al., "Sphingosine–1–phosphate: Extracellular Mediator or Intracellular Second Messenger?" *Biochemical Pharmacology*, 58:201–207 (1999).
Kohama, et al., "Molecular Cloning and Functional Characterization of Murine Sphingosine Kinase," *The Journal of Biological Chemistry*, 273(37):23722–23728 (Sep. 11, 1998).
Lee, et al., "Sphingosine–1–Phosphate as a Ligand for the G Protein–Coupled Receptor EDG–1," *Science*, 279:1552–1555 (Mar. 6, 1998).
Lee, et al., "Vascular Endothelial Cell Adherens Junction Assembly and Morphogenesis Induced by Sphingosine–1–Phosphate," *Cell*, 99:301–312 (Oct. 29, 1999).

Lee, et al., "Sphingosine 1–Phosphate Induces Angiogenesis: Its Angiogenic Action and Signaling Mechanism in Human Umbilical Vein Endothelial Cells," *Biochemical and Biophysical Research Communications*, 264:743–750 (1999).
Liau, G., "A Gene Therapy Approach toward the Modulation of Angiogenesis," International Business Communications Sixth Annual International Conference on Angiogenesis, Oct. 5–6, 2000.
Liu, et al., "Molecular Cloning and Functional Characterization of a Novel Mammalian Sphingosine Kinase Type 2 Isoform," *The Journal of Biological Chemistry*, 275(26):19513–19520 (Jun. 30, 2000).
Liu, et al., "Edg–1, the G Protein–Coupled Receptor for Sphingosine–1–Phosphate, is Essential for Vascular Maturation," *The Journal of Clinical Investigation*, 106(8):951–961 (Oct. 2000).
Nava, et al., "Functional Characterization of Human Sphingosine Kinase–1," *FEBS Letters*, 473:81–84 (May 4, 2000).
Olivera, et al., "Sphingosine–1–Phosphate as Second Messenger in Cell Proliferation Induced by PDGF and FCS Mitogens," *Nature*, 365:557–560 (Oct. 7, 1993).
Panetti, et al., "Sphingosine–1–Phosphate and Lysophosphatidic Acid Stimulate Endothelial Cell Migration," *Arterioscler. Thromb. Vasc. Biol.*, pp. 1013–1019 (1999).
Passaniti, et al., "Methods in Laboratory Investigation," *Laboratory Investigation*, 67(4):519–528 (1992).
Pyne, et al., "Sphingosine 1–Phosphate Signalling in Mammalian Cells," *Biochem., J.*, 349:385–402 (Jul. 15, 2000).
Spiegel, S., "Sphingosine 1–Phosphate: A Prototype of a New Class of Second Messengers," *Journal of Leukocyte Biology*, 65:341–344 (Mar. 1999).
Wang, et al., "Sphingosine 1–Phosphate Stimulates Cell Migration Through a $G_i$–Coupled Cell Surface Receptor," *The Journal of Biological Chemistry*, 274(50):35343–35350 (Dec. 10, 1999).
Ylä–Herttuala, et al., "Cardiovascular Gene Therapy," *The Lancet*, 355:213–222 (Jan. 15, 2000).
Zhang, et al., "Comparative Analysis of Three Murine G–Protein Coupled Receptors Activated by Sphingosine–1–Phosphate," *Gene*, 227:89–99 (1999).
Banno, et al., "Evidence for the Presence of Multiple Forms of Sph Kinase in Human Platelets," *J. Biochem.*, 335:301–304 (1998).

* cited by examiner

Primary Examiner—Dave T. Nguyen
Assistant Examiner—J Eric Angell
(74) Attorney, Agent, or Firm—J. Timothy Meigs; Douglas A. Golightly; Geoffrey M. Karny

(57) ABSTRACT

A method of inducing blood vessel formation in an animal by administering to the animal a polynucleotide encoding a sphingosine kinase, or an analogue, fragment, or derivative thereof. The polynucleotide may be contained in an appropriate expression vector, such as a viral vector. The delivery of sphingosine kinase through administration of an expression vector which expresses sphingosine kinase provides for the formation of larger blood vessels containing a well defined structure that is supported by mural cells such as pericytes and smooth muscle cells.

12 Claims, 7 Drawing Sheets

```
  1  ATG GAA CCA GTA GAA TGC CCT CGA GGA CTG CTC CCA
     Met Glu Pro Val Glu Cys Pro Arg Gly Leu Leu Pro

37  CGG CCA TGC AGA GTG CTG GTG CTG CTG AAC CCC CAG
     Arg Pro Cys Arg Val Leu Val Leu Leu Asn Pro Gln

73  GGT GGC AAG GGC AAG GCT CTG CAG CTC TTC CAG AGC
     Gly Gly Lys Gly Lys Ala Leu Gln Leu Phe Gln Ser

109  CGT GTG CAG CCC TTC CTG GAG GAG GCA GAG ATA ACC
     Arg Val Gln Pro Phe Leu Glu Glu Ala Glu Ile Thr

145  TTT AAA CTG ATA CTC ACC GAA CGG AAG AAC CAT GCC
     Phe Lys Leu Ile Leu Thr Glu Arg Lys Asn His Ala

181  AGG GAG CTG GTG TGT GCA GAG GAG TTG GGT CAC TGG
     Arg Glu Leu Val Cys Ala Glu Glu Leu Gly His Trp

217  GAC GCC CTG GCA GTC ATG TCC GGT GAT GGT CTG ATG
     Asp Ala Leu Ala Val Met Ser Gly Asp Gly Leu Met

253  CAT GAG GTG GTG AAT GGG CTA ATG GAA CGG CCC GAC
     His Glu Val Val Asn Gly Leu Met Glu Arg Pro Asp

289  TGG GAG ACT GCC ATC CAG AAA CCC CTG TGT AGC CTC
     Trp Glu Thr Ala Ile Gln Lys Pro Leu Cys Ser Leu

325  CCT GGA GGC TCC GGC AAT GCG CTG GCA GCT TCT GTG
     Pro Gly Gly Ser Gly Asn Ala Leu Ala Ala Ser Val

361  AAC CAC TAT GCT GGG TAC GAG CAG GTG ACT AAT GAA
     Asn His Tyr Ala Gly Tyr Glu Gln Val Thr Asn Glu

397  GAC CTG CTC ATC AAC TGC ACA CTG CTG TTG TGC CGC
     Asp Leu Leu Ile Asn Cys Thr Leu Leu Leu Cys Arg

433  CGG CGC CTG TCA CCC ATG AAC CTG CTG TCC CTG CAC
     Arg Arg Leu Ser Pro Met Asn Leu Leu Ser Leu His

469  ACT GCT TCT GGG CTG CGG CTC TAT TCT GTG CTC AGT
     Thr Ala Ser Gly Leu Arg Leu Tyr Ser Val Leu Ser

505  CTG TCC TGG GGC TTT GTT GCT GAC GTG GAC CTC GAG
     Leu Ser Trp Gly Phe Val Ala Asp Val Asp Leu Glu

541  AGT GAG AAG TAC AGG CGC TTG GGG GAG ATT CGT TTC
     Ser Glu Lys Tyr Arg Arg Leu Gly Glu Ile Arg Phe

577  ACA GTG GGC ACC TTC TTT CGC CTA GCA AGC CTG CGC
     Thr Val Gly Thr Phe Phe Arg Leu Ala Ser Leu Arg

613  ATC TAC CAA GGC CAA CTG GCC TAC CTT CCT GTA GGA
     Ile Tyr Gln Gly Gln Leu Ala Tyr Leu Pro Val Gly

649  ACT GTG GCC TCT AAG AGA CCC GCC TCT ACA CTG GTG
     Thr Val Ala Ser Lys Arg Pro Ala Ser Thr Leu Val

685  CAG AAG GGC CCC GTC GAC ACA CAC CTT GTT CCT CTG
     Gln Lys Gly Pro Val Asp Thr His Leu Val Pro Leu

721  GAG GAG CCA GTG CCT TCT CAT TGG ACT GTG GTA CCA
```

FIG 2

```
        Glu Glu Pro Val Pro Ser His Trp Thr Val Val Pro
 757    GAA CAG GAC TTT GTC CTG GTG CTG GTG CTG CTA CAC
        Glu Gln Asp Phe Val Leu Val Leu Val Leu Leu His

793    ACC CAC CTG AGC TCC GAG CTG TTT GCA GCA CCC ATG
        Thr His Leu Ser Ser Glu Leu Phe Ala Ala Pro Met

829    GGC CGC TGT GAG GCT GGT GTT ATG CAT CTG TTC TAC
        Gly Arg Cys Glu Ala Gly Val Met His Leu Phe Tyr

865    GTA CGT GCG GGG GTG TCA AGG GCT GCG CTG CTG CGC
        Val Arg Ala Gly Val Ser Arg Ala Ala Leu Leu Arg

901    CTC TTC CTG GCC ATG CAG AAG GGC AAG CAT ATG GAA
        Leu Phe Leu Ala Met Gln Lys Gly Lys His Met Glu

937    CTT GAC TGT CCA TAC CTG GTT CAT GTG CCC GTG GTT
        Leu Asp Cys Pro Tyr Leu Val His Val Pro Val Val

973    GCT TTC CGC CTG GAG CCC AGG AGC CAG AGG GGC GTG
        Ala Phe Arg Leu Glu Pro Arg Ser Gln Arg Gly Val

1009    TTT TCT GTG GAT GGA GGG CTG ATG GTA TGT GAA GCT
        Phe Ser Val Asp Gly Gly Leu Met Val Cys Glu Ala

1045    GTG CAG GGC CAA GTG CAC CCA AAC TAC CTT TGG ATG
        Val Gln Gly Gln Val His Pro Asn Tyr Leu Trp Met

1081    GTC TGT GGC AGC AGA GAT GCC CCA TCC GGC CGG GAC
        Val Cys Gly Ser Arg Asp Ala Pro Ser Gly Arg Asp

1117    TCC CGG CGG GGG CCA CCT CCA GAA GAA CCA TAA  (Seq ID:5)
        Ser Arg Arg Gly Pro Pro Pro Glu Glu Pro ---  (Seq ID:6)
```

Figure 2 (Cont)

SEQUENCE LISTING

```
<160> NUMBER OF SEQ ID NOS: 6

<210> SEQ ID NO 1
<211> LENGTH: 1155
<212> TYPE: DNA
<213> ORGANISM: Homo sapiens
<220> FEATURE:
<221> NAME/KEY: CDS
<222> LOCATION: (1)..(1155)
<223> OTHER INFORMATION:

<400> SEQUENCE: 1 atg gat cca gcg ggc ggc ccc cgg ggc gtg ctc ccg cgg ccc tgc cgc      48
Met Asp Pro Ala Gly Gly Pro Arg Gly Val Leu Pro Arg Pro Cys Arg
1               5                   10                  15 gtg ctg gtg ctg ctg aac ccg cgc ggc ggc aag ggc aag gcc ttg cag      96
Val Leu Val Leu Leu Asn Pro Arg Gly Gly Lys Gly Lys Ala Leu Gln
                20                  25                  30 ctc ttc cgg agt cac gtg cag ccc ctt ttg gct gag gct gaa atc tcc     144
Leu Phe Arg Ser His Val Gln Pro Leu Leu Ala Glu Ala Glu Ile Ser
            35                  40                  45 ttc acg ctg atg ctc act gag cgg cgg aac cac gcg cgg gag ctg gtg     192
Phe Thr Leu Met Leu Thr Glu Arg Arg Asn His Ala Arg Glu Leu Val
        50                  55                  60 cgg tcg gag gag ctg ggc cgc tgg gac gct ctg gtg gtc atg tct gga     240
Arg Ser Glu Glu Leu Gly Arg Trp Asp Ala Leu Val Val Met Ser Gly
65                  70                  75                  80 gac ggg ctg atg cac gag gtg gtg aac ggg ctc atg gag cgg cct gac     288
Asp Gly Leu Met His Glu Val Val Asn Gly Leu Met Glu Arg Pro Asp
                85                  90                  95 tgg gag acc gcc atc cag aag ccc ctg tgt agc ctc cca gca ggc tct     336
Trp Glu Thr Ala Ile Gln Lys Pro Leu Cys Ser Leu Pro Ala Gly Ser
            100                 105                 110 ggc aac gcg ctg gca gct tcc ttg aac cat tat gct ggc tat gag cag     384
Gly Asn Ala Leu Ala Ala Ser Leu Asn His Tyr Ala Gly Tyr Glu Gln
        115                 120                 125
```

-continued

```
gtc acc aat gaa gac ctc ctg acc aac tgc acg cta ttg ctg tgc cgc      432
Val Thr Asn Glu Asp Leu Leu Thr Asn Cys Thr Leu Leu Cys Arg
    130                 135                 140 cgg ctg ctg tca ccc atg aac ctg ctg tct ctg cac acg gct tcg ggg      480
Arg Leu Leu Ser Pro Met Asn Leu Leu Ser Leu His Thr Ala Ser Gly
145                 150                 155                 160 ctg cgc ctc ttc tct gtg ctc agc ctg gcc tgg ggc ttc att gct gat      528
Leu Arg Leu Phe Ser Val Leu Ser Leu Ala Trp Gly Phe Ile Ala Asp
                165                 170                 175 gtg gac cta gag agt gag aag tat cgg cgt ctg ggg gag atg cgc ttc      576
Val Asp Leu Glu Ser Glu Lys Tyr Arg Arg Leu Gly Glu Met Arg Phe
            180                 185                 190 act ctg ggc acc ttc ctg cgt ctg gca gcc ctg cgc acc tac cgc ggc      624
Thr Leu Gly Thr Phe Leu Arg Leu Ala Ala Leu Arg Thr Tyr Arg Gly
        195                 200                 205 cga ctg gcc tac ctc cct gta gga aga gtg ggt tcc aag aca cct gcc      672
Arg Leu Ala Tyr Leu Pro Val Gly Arg Val Gly Ser Lys Thr Pro Ala
    210                 215                 220 tcc ccc gtt gtg gtc cag cag ggc ccg gta gat gca cac ctt gtg cca      720
Ser Pro Val Val Val Gln Gln Gly Pro Val Asp Ala His Leu Val Pro
225                 230                 235                 240 ctg gag gag cca gtg ccc tct cac tgg aca gtg gtg ccc gac gag gac      768
Leu Glu Glu Pro Val Pro Ser His Trp Thr Val Val Pro Asp Glu Asp
                245                 250                 255 ttt gtg cta gtc ctg gca ctg ctg cac tcg cac ctg ggc agt gag atg      816
Phe Val Leu Val Leu Ala Leu Leu His Ser His Leu Gly Ser Glu Met
            260                 265                 270 ttt gct gca ccc atg ggc cgc tgt gca gct ggc gtc atg cat ctg ttc      864
Phe Ala Ala Pro Met Gly Arg Cys Ala Ala Gly Val Met His Leu Phe
        275                 280                 285 tac gtg cgg gcg gga gtg tct cgt gcc atg ctg ctg cgc ctc ttc ctg      912
Tyr Val Arg Ala Gly Val Ser Arg Ala Met Leu Leu Arg Leu Phe Leu
    290                 295                 300 gcc atg gag aag ggc agg cat atg gag tat gaa tgc ccc tac ttg gta      960
Ala Met Glu Lys Gly Arg His Met Glu Tyr Glu Cys Pro Tyr Leu Val
305                 310                 315                 320 tat gtg ccc gtg gtc gcc ttc cgc ttg gag ccc aag gat ggg aaa ggt     1008
Tyr Val Pro Val Val Ala Phe Arg Leu Glu Pro Lys Asp Gly Lys Gly
                325                 330                 335 gtg ttt gca gtg gat ggg gaa ttg atg gtt agc gag gcc gtg cag ggc     1056
Val Phe Ala Val Asp Gly Glu Leu Met Val Ser Glu Ala Val Gln Gly
            340                 345                 350 cag gtg cac cca aac tac ttc tgg atg gtc agc ggt tgc gtg gag ccc     1104
Gln Val His Pro Asn Tyr Phe Trp Met Val Ser Gly Cys Val Glu Pro
        355                 360                 365 ccg ccc agc tgg aag ccc cag cag atg cca ccg cca gaa gag ccc tta     1152
Pro Pro Ser Trp Lys Pro Gln Gln Met Pro Pro Pro Glu Glu Pro Leu
    370                 375                 380 tga                                                                  1155

SEQ ID NO 2
LENGTH: 384
TYPE: PRT

<213> ORGANISM: Homo sapiens

<400> SEQUENCE: 2

Met Asp Pro Ala Gly Gly Pro Arg Gly Val Leu Pro Arg Pro Cys Arg
1               5                   10                  15
```

```
Val Leu Val Leu Leu Asn Pro Arg Gly Lys Gly Lys Ala Leu Gln
            20                  25                  30

Leu Phe Arg Ser His Val Gln Pro Leu Leu Ala Glu Ala Glu Ile Ser
        35                  40                  45

Phe Thr Leu Met Leu Thr Glu Arg Arg Asn His Ala Arg Glu Leu Val
    50                  55                  60

Arg Ser Glu Glu Leu Gly Arg Trp Asp Ala Leu Val Val Met Ser Gly
65                  70                  75                  80

Asp Gly Leu Met His Glu Val Val Asn Gly Leu Met Glu Arg Pro Asp
                85                  90                  95

Trp Glu Thr Ala Ile Gln Lys Pro Leu Cys Ser Leu Pro Ala Gly Ser
            100                 105                 110

Gly Asn Ala Leu Ala Ala Ser Leu Asn His Tyr Ala Gly Tyr Glu Gln
        115                 120                 125

Val Thr Asn Glu Asp Leu Leu Thr Asn Cys Thr Leu Leu Leu Cys Arg
    130                 135                 140

Arg Leu Leu Ser Pro Met Asn Leu Leu Ser Leu His Thr Ala Ser Gly
145                 150                 155                 160

Leu Arg Leu Phe Ser Val Leu Ser Leu Ala Trp Gly Phe Ile Ala Asp
                165                 170                 175

Val Asp Leu Glu Ser Glu Lys Tyr Arg Arg Leu Gly Glu Met Arg Phe
            180                 185                 190

Thr Leu Gly Thr Phe Leu Arg Leu Ala Ala Leu Arg Thr Tyr Arg Gly
        195                 200                 205

Arg Leu Ala Tyr Leu Pro Val Gly Arg Val Gly Ser Lys Thr Pro Ala
    210                 215                 220

Ser Pro Val Val Val Gln Gln Gly Pro Val Asp Ala His Leu Val Pro
225                 230                 235                 240

Leu Glu Glu Pro Val Pro Ser His Trp Thr Val Val Pro Asp Glu Asp
                245                 250                 255

Phe Val Leu Val Leu Ala Leu Leu His Ser His Leu Gly Ser Glu Met
            260                 265                 270

Phe Ala Ala Pro Met Gly Arg Cys Ala Ala Gly Val Met His Leu Phe
        275                 280                 285

Tyr Val Arg Ala Gly Val Ser Arg Ala Met Leu Leu Arg Leu Phe Leu
    290                 295                 300

Ala Met Glu Lys Gly Arg His Met Glu Tyr Glu Cys Pro Tyr Leu Val
305                 310                 315                 320

Tyr Val Pro Val Val Ala Phe Arg Leu Glu Pro Lys Asp Gly Lys Gly
                325                 330                 335

Val Phe Ala Val Asp Gly Glu Leu Met Val Ser Glu Ala Val Gln Gly
            340                 345                 350

Gln Val His Pro Asn Tyr Phe Trp Met Val Ser Gly Cys Val Glu Pro
        355                 360                 365

Pro Pro Ser Trp Lys Pro Gln Gln Met Pro Pro Glu Glu Pro Leu
    370                 375                 380
```

<210> SEQ ID NO 3
<211> LENGTH: 1857
<212> TYPE: DNA
<213> ORGANISM: Homo sapiens
<220> FEATURE:
<221> NAME/KEY: CDS
<222> LOCATION: (1)..(1857)
<223> OTHER INFORMATION:

<400> SEQUENCE: 3

```
atg gcc ccg ccc cca ccg cca ctg gct gcc agc acc ccg ctc ctc cat    48
Met Ala Pro Pro Pro Pro Leu Ala Ala Ser Thr Pro Leu Leu His
 1               5                  10                  15 ggc gag ttt ggc tcc tac cca gcc cga ggc cca cgt ttt gcc ctc acc    96
Gly Glu Phe Gly Ser Tyr Pro Ala Arg Gly Pro Arg Phe Ala Leu Thr
                20                  25                  30 ctt aca tcg cag gcc ctg cac ata cag cgg ctg cgc ccc aaa cct gaa   144
Leu Thr Ser Gln Ala Leu His Ile Gln Arg Leu Arg Pro Lys Pro Glu
            35                  40                  45 gcc agg ccc cgg ggt ggc ctg gtc ccg ttg gcc gag gtc tca ggc tgc   192
Ala Arg Pro Arg Gly Gly Leu Val Pro Leu Ala Glu Val Ser Gly Cys
        50                  55                  60 tgc acc ctg cga agc cgc agc ccc tca gac tca gcg gcc tac ttc tgc   240
Cys Thr Leu Arg Ser Arg Ser Pro Ser Asp Ser Ala Ala Tyr Phe Cys
 65                 70                  75                  80 atc tac acc tac cct cgg ggc cgg cgc ggg gcc cgg cgc aga gcc act   288
Ile Tyr Thr Tyr Pro Arg Gly Arg Arg Gly Ala Arg Arg Arg Ala Thr
                85                  90                  95 cgc acc ttc cgg gca gat ggg gcc gcc acc tac gaa gag aac cgt gcc   336
Arg Thr Phe Arg Ala Asp Gly Ala Ala Thr Tyr Glu Glu Asn Arg Ala
            100                 105                 110 gag gcc cag cgc tgg gcc act gcc ctc acc tgt ctg ctc cga gga ctg   384
Glu Ala Gln Arg Trp Ala Thr Ala Leu Thr Cys Leu Leu Arg Gly Leu
        115                 120                 125 cca ctg ccc ggg gat ggg gag atc acc cct gac ctg cta cct cgg ccg   432
Pro Leu Pro Gly Asp Gly Glu Ile Thr Pro Asp Leu Leu Pro Arg Pro
    130                 135                 140 ccc cgg ttg ctt cta ttg gtc aat ccc ttt ggg ggt cgg ggc ctg gcc   480
Pro Arg Leu Leu Leu Leu Val Asn Pro Phe Gly Gly Arg Gly Leu Ala
145                 150                 155                 160 tgg cag tgg tgt aag aac cac gtg ctt ccc atg atc tct gaa gct ggg   528
Trp Gln Trp Cys Lys Asn His Val Leu Pro Met Ile Ser Glu Ala Gly
                165                 170                 175 ctg tcc ttc aac ctc atc cag aca gaa cga cag aac cac gcc cgg gag   576
Leu Ser Phe Asn Leu Ile Gln Thr Glu Arg Gln Asn His Ala Arg Glu
            180                 185                 190 ctg gtc cag ggg ctg agc ctg agt gag tgg gat ggc atc gtc acg gtc   624
Leu Val Gln Gly Leu Ser Leu Ser Glu Trp Asp Gly Ile Val Thr Val
        195                 200                 205 tcg gga gac ggg ctg ctc cat gag gtg ctg aac ggg ctc cta gat cgc   672
Ser Gly Asp Gly Leu Leu His Glu Val Leu Asn Gly Leu Leu Asp Arg
    210                 215                 220 cct gac tgg gag gaa gct gtg aag atg cct gtg ggc atc ctc ccc tgc   720
Pro Asp Trp Glu Glu Ala Val Lys Met Pro Val Gly Ile Leu Pro Cys
225                 230                 235                 240 ggc tcg ggc aac gcg ctg gcc gga gca gtg aac cag cac ggg gga ttt   768
Gly Ser Gly Asn Ala Leu Ala Gly Ala Val Asn Gln His Gly Gly Phe
                245                 250                 255 gag cca gcc ctg ggc ctc gac ctg ttg ctc aac tgc tca ctg ttg ctg   816
Glu Pro Ala Leu Gly Leu Asp Leu Leu Leu Asn Cys Ser Leu Leu Leu
            260                 265                 270 tgc cgg ggt ggt ggc cac cca ctg gac ctg ctc tcc gtg acg ctg gcc   864
Cys Arg Gly Gly Gly His Pro Leu Asp Leu Leu Ser Val Thr Leu Ala
        275                 280                 285 tcg ggc tcc cgc tgt ttc tcc ttc ctg tct gtg gcc tgg ggc ttc gtg   912
Ser Gly Ser Arg Cys Phe Ser Phe Leu Ser Val Ala Trp Gly Phe Val
    290                 295                 300 tca gat gtg gat atc cag agc gag cgc ttc agg gcc ttg ggc agt gcc   960
```

-continued

```
Ser Asp Val Asp Ile Gln Ser Glu Arg Phe Arg Ala Leu Gly Ser Ala
305                 310                 315                 320 cgc ttc aca ctg ggc acg gtg ctg ggc ctc gcc aca ctg cac acc tac    1008
Arg Phe Thr Leu Gly Thr Val Leu Gly Leu Ala Thr Leu His Thr Tyr
                325                 330                 335 cgc gga cgc ctc tcc tac ctc ccc gcc act gtg gaa cct gcc tcg ccc    1056
Arg Gly Arg Leu Ser Tyr Leu Pro Ala Thr Val Glu Pro Ala Ser Pro
            340                 345                 350 acc cct gcc cat agc ctg cct cgt gcc aag tcg gag ctg acc cta acc    1104
Thr Pro Ala His Ser Leu Pro Arg Ala Lys Ser Glu Leu Thr Leu Thr
        355                 360                 365 cca gac cca gcc ccg ccc atg gcc cac tca ccc ctg cat cgt tct gtg    1152
Pro Asp Pro Ala Pro Pro Met Ala His Ser Pro Leu His Arg Ser Val
    370                 375                 380 tct gac ctg cct ctt ccc ctg ccc cag cct gcc ctg gcc tct cct ggc    1200
Ser Asp Leu Pro Leu Pro Leu Pro Gln Pro Ala Leu Ala Ser Pro Gly
385                 390                 395                 400 tcg cca gaa ccc ctg ccc atc ctg tcc ctc aac ggt ggg ggc cca gag    1248
Ser Pro Glu Pro Leu Pro Ile Leu Ser Leu Asn Gly Gly Gly Pro Glu
                405                 410                 415 ctg gct ggg gac tgg ggt ggg gct ggg gat gct ccg ctg tcc ccg gac    1296
Leu Ala Gly Asp Trp Gly Gly Ala Gly Asp Ala Pro Leu Ser Pro Asp
            420                 425                 430 cca ctg ctg tct tca cct cct ggc tct ccc aag gca gct cta cac tca    1344
Pro Leu Leu Ser Ser Pro Pro Gly Ser Pro Lys Ala Ala Leu His Ser
        435                 440                 445 ccc gtc tcc gaa ggg gcc ccc gta att ccc cca tcc tct ggg ctc cca    1392
Pro Val Ser Glu Gly Ala Pro Val Ile Pro Pro Ser Ser Gly Leu Pro
    450                 455                 460 ctt ccc acc cct gat gcc cgg gta ggg gcc tcc acc tgc ggc ccg ccc    1440
Leu Pro Thr Pro Asp Ala Arg Val Gly Ala Ser Thr Cys Gly Pro Pro
465                 470                 475                 480 gac cac ctg ctg cct ccg ctg ggc acc ccg ctg ccc cca gac tgg gtg    1488
Asp His Leu Leu Pro Pro Leu Gly Thr Pro Leu Pro Pro Asp Trp Val
                485                 490                 495 acg ctg gag ggg gac ttt gtg ctc atg ttg gcc atc tcg ccc agc cac    1536
Thr Leu Glu Gly Asp Phe Val Leu Met Leu Ala Ile Ser Pro Ser His
            500                 505                 510 cta ggc gct gac ctg gtg gca gct ccg cat gcg cgc ttc gac gac ggc    1584
Leu Gly Ala Asp Leu Val Ala Ala Pro His Ala Arg Phe Asp Asp Gly
        515                 520                 525 ctg gtg cac ctg tgc tgg gtg cgt agc ggc atc tcg cgg gct gcg ctg    1632
Leu Val His Leu Cys Trp Val Arg Ser Gly Ile Ser Arg Ala Ala Leu
    530                 535                 540 ctg cgc ctt ttc ttg gcc atg gag cgt ggt agc cac ttc agc ctg ggc    1680
Leu Arg Leu Phe Leu Ala Met Glu Arg Gly Ser His Phe Ser Leu Gly
545                 550                 555                 560 tgt ccg cag ctg ggc tac gcc gcg gcc cgt gcc ttc cgc cta gag ccg    1728
Cys Pro Gln Leu Gly Tyr Ala Ala Ala Arg Ala Phe Arg Leu Glu Pro
                565                 570                 575 ctc aca cca cgc ggc gtg ctc aca gtg gac ggg gag cag gtg gag tat    1776
Leu Thr Pro Arg Gly Val Leu Thr Val Asp Gly Glu Gln Val Glu Tyr
            580                 585                 590 ggg ccg cta cag gca cag atg cac cct ggc atc ggt aca ctg ctc act    1824
Gly Pro Leu Gln Ala Gln Met His Pro Gly Ile Gly Thr Leu Leu Thr
        595                 600                 605 ggg cct cct ggc tgc ccg ggg cgg gag ccc tga                        1857
Gly Pro Pro Gly Cys Pro Gly Arg Glu Pro
    610                 615
```

```
<210> SEQ ID NO 4
<211> LENGTH: 618
<212> TYPE: PRT
<213> ORGANISM: Homo sapiens

<400> SEQUENCE: 4

Met Ala Pro Pro Pro Pro Leu Ala Ala Ser Thr Pro Leu Leu His
1               5                   10                  15

Gly Glu Phe Gly Ser Tyr Pro Ala Arg Gly Pro Arg Phe Ala Leu Thr
                20                  25                  30

Leu Thr Ser Gln Ala Leu His Ile Gln Arg Leu Arg Pro Lys Pro Glu
            35                  40                  45

Ala Arg Pro Arg Gly Gly Leu Val Pro Leu Ala Glu Val Ser Gly Cys
        50                  55                  60

Cys Thr Leu Arg Ser Arg Ser Pro Ser Asp Ser Ala Ala Tyr Phe Cys
65                  70                  75                  80

Ile Tyr Thr Tyr Pro Arg Gly Arg Arg Gly Ala Arg Arg Ala Thr
                85                  90                  95

Arg Thr Phe Arg Ala Asp Gly Ala Ala Thr Tyr Glu Glu Asn Arg Ala
                100                 105                 110

Glu Ala Gln Arg Trp Ala Thr Ala Leu Thr Cys Leu Leu Arg Gly Leu
            115                 120                 125

Pro Leu Pro Gly Asp Gly Glu Ile Thr Pro Asp Leu Leu Pro Arg Pro
        130                 135                 140

Pro Arg Leu Leu Leu Leu Val Asn Pro Phe Gly Gly Arg Gly Leu Ala
145                 150                 155                 160

Trp Gln Trp Cys Lys Asn His Val Leu Pro Met Ile Ser Glu Ala Gly
                165                 170                 175

Leu Ser Phe Asn Leu Ile Gln Thr Glu Arg Gln Asn His Ala Arg Glu
                180                 185                 190

Leu Val Gln Gly Leu Ser Leu Ser Glu Trp Asp Gly Ile Val Thr Val
            195                 200                 205

Ser Gly Asp Gly Leu Leu His Glu Val Leu Asn Gly Leu Leu Asp Arg
        210                 215                 220

Pro Asp Trp Glu Glu Ala Val Lys Met Pro Val Gly Ile Leu Pro Cys
225                 230                 235                 240

Gly Ser Gly Asn Ala Leu Ala Gly Ala Val Asn Gln His Gly Gly Phe
                245                 250                 255

Glu Pro Ala Leu Gly Leu Asp Leu Leu Asn Cys Ser Leu Leu Leu
                260                 265                 270

Cys Arg Gly Gly His Pro Leu Asp Leu Leu Ser Val Thr Leu Ala
            275                 280                 285

Ser Gly Ser Arg Cys Phe Ser Phe Leu Ser Val Ala Trp Gly Phe Val
        290                 295                 300

Ser Asp Val Asp Ile Gln Ser Glu Arg Phe Arg Ala Leu Gly Ser Ala
305                 310                 315                 320

Arg Phe Thr Leu Gly Thr Val Leu Gly Leu Ala Thr Leu His Thr Tyr
                325                 330                 335

Arg Gly Arg Leu Ser Tyr Leu Pro Ala Thr Val Glu Pro Ala Ser Pro
                340                 345                 350

Thr Pro Ala His Ser Leu Pro Arg Ala Lys Ser Glu Leu Thr Leu Thr
            355                 360                 365

Pro Asp Pro Ala Pro Pro Met Ala His Ser Pro Leu His Arg Ser Val
        370                 375                 380
```

```
Ser Asp Leu Pro Leu Pro Leu Pro Gln Pro Ala Leu Ala Ser Pro Gly
385                 390                 395                 400

Ser Pro Glu Pro Leu Pro Ile Leu Ser Leu Asn Gly Gly Gly Pro Glu
            405                 410                 415

Leu Ala Gly Asp Trp Gly Gly Ala Gly Asp Ala Pro Leu Ser Pro Asp
                420                 425                 430

Pro Leu Leu Ser Ser Pro Pro Gly Ser Pro Lys Ala Ala Leu His Ser
            435                 440                 445

Pro Val Ser Glu Gly Ala Pro Val Ile Pro Pro Ser Ser Gly Leu Pro
        450                 455                 460

Leu Pro Thr Pro Asp Ala Arg Val Gly Ala Ser Thr Cys Gly Pro Pro
465                 470                 475                 480

Asp His Leu Leu Pro Pro Leu Gly Thr Pro Leu Pro Pro Asp Trp Val
                485                 490                 495

Thr Leu Glu Gly Asp Phe Val Leu Met Leu Ala Ile Ser Pro Ser His
                500                 505                 510

Leu Gly Ala Asp Leu Val Ala Ala Pro His Ala Arg Phe Asp Asp Gly
        515                 520                 525

Leu Val His Leu Cys Trp Val Arg Ser Gly Ile Ser Arg Ala Ala Leu
    530                 535                 540

Leu Arg Leu Phe Leu Ala Met Glu Arg Gly Ser His Phe Ser Leu Gly
545                 550                 555                 560

Cys Pro Gln Leu Gly Tyr Ala Ala Ala Arg Ala Phe Arg Leu Glu Pro
                565                 570                 575

Leu Thr Pro Arg Gly Val Leu Thr Val Asp Gly Glu Gln Val Glu Tyr
            580                 585                 590

Gly Pro Leu Gln Ala Gln Met His Pro Gly Ile Gly Thr Leu Leu Thr
        595                 600                 605

Gly Pro Pro Gly Cys Pro Gly Arg Glu Pro
    610                 615

<210> SEQ ID NO 5
<211> LENGTH: 1149
<212> TYPE: DNA
<213> ORGANISM: Mus musculus
<220> FEATURE:
<221> NAME/KEY: CDS
<222> LOCATION: (1)..(1149)
<223> OTHER INFORMATION:

<400> SEQUENCE: 5 atg gaa cca gta gaa tgc cct cga gga ctg ctc cca cgg cca tgc aga      48
Met Glu Pro Val Glu Cys Pro Arg Gly Leu Leu Pro Arg Pro Cys Arg
1               5                   10                  15 gtg ctg gtg ctg ctg aac ccc cag ggt ggc aag ggc aag gct ctg cag      96
Val Leu Val Leu Leu Asn Pro Gln Gly Gly Lys Gly Lys Ala Leu Gln
            20                  25                  30 ctc ttc cag agc cgt gtg cag ccc ttc ctg gag gag gca gag ata acc     144
Leu Phe Gln Ser Arg Val Gln Pro Phe Leu Glu Glu Ala Glu Ile Thr
        35                  40                  45 ttt aaa ctg ata ctc acc gaa cgg aag aac cat gcc agg gag ctg gtg     192
Phe Lys Leu Ile Leu Thr Glu Arg Lys Asn His Ala Arg Glu Leu Val
    50                  55                  60 tgt gca gag gag ttg ggt cac tgg gac gcc ctg gca gtc atg tcc ggt     240
Cys Ala Glu Glu Leu Gly His Trp Asp Ala Leu Ala Val Met Ser Gly
65                  70                  75                  80 gat ggt ctg atg cat gag gtg gtg aat ggg cta atg gaa cgg ccc gac     288
```

```
                    Asp Gly Leu Met His Glu Val Val Asn Gly Leu Met Glu Arg Pro Asp
                                    85                  90                  95 tgg gag act gcc atc cag aaa ccc ctg tgt agc ctc cct gga ggc tcc              336
Trp Glu Thr Ala Ile Gln Lys Pro Leu Cys Ser Leu Pro Gly Gly Ser
                100                 105                 110 ggc aat gcg ctg gca gct tct gtg aac cac tat gct ggg tac gag cag              384
Gly Asn Ala Leu Ala Ala Ser Val Asn His Tyr Ala Gly Tyr Glu Gln
            115                 120                 125 gtg act aat gaa gac ctg ctc atc aac tgc aca ctg ctg ttg tgc cgc              432
Val Thr Asn Glu Asp Leu Leu Ile Asn Cys Thr Leu Leu Leu Cys Arg
        130                 135                 140 cgg cgc ctg tca ccc atg aac ctg ctg tcc ctg cac act gct tct ggg              480
Arg Arg Leu Ser Pro Met Asn Leu Leu Ser Leu His Thr Ala Ser Gly
145                 150                 155                 160 ctg cgg ctc tat tct gtg ctc agt ctg tcc tgg ggc ttt gtt gct gac              528
Leu Arg Leu Tyr Ser Val Leu Ser Leu Ser Trp Gly Phe Val Ala Asp
                165                 170                 175 gtg gac ctc gag agt gag aag tac agg cgc ttg ggg gag att cgt ttc              576
Val Asp Leu Glu Ser Glu Lys Tyr Arg Arg Leu Gly Glu Ile Arg Phe
            180                 185                 190 aca gtg ggc acc ttc ttt cgc cta gca agc ctg cgc atc tac caa ggc              624
Thr Val Gly Thr Phe Phe Arg Leu Ala Ser Leu Arg Ile Tyr Gln Gly
        195                 200                 205 caa ctg gcc tac ctt cct gta gga act gtg gcc tct aag aga ccc gcc              672
Gln Leu Ala Tyr Leu Pro Val Gly Thr Val Ala Ser Lys Arg Pro Ala
    210                 215                 220 tct aca ctg gtg cag aag ggc ccc gtc gac aca cac ctt gtt cct ctg              720
Ser Thr Leu Val Gln Lys Gly Pro Val Asp Thr His Leu Val Pro Leu
225                 230                 235                 240 gag gag cca gtg cct tct cat tgg act gtg gta cca gaa cag gac ttt              768
Glu Glu Pro Val Pro Ser His Trp Thr Val Val Pro Glu Gln Asp Phe
                245                 250                 255 gtc ctg gtg ctg gtg ctg cta cac acc cac ctg agc tcc gag ctg ttt              816
Val Leu Val Leu Val Leu Leu His Thr His Leu Ser Ser Glu Leu Phe
            260                 265                 270 gca gca ccc atg ggc cgc tgt gag gct ggt gtt atg cat ctg ttc tac              864
Ala Ala Pro Met Gly Arg Cys Glu Ala Gly Val Met His Leu Phe Tyr
        275                 280                 285 gta cgt gcg ggg gtg tca agg gct gcg ctg ctg cgc ctc ttc ctg gcc              912
Val Arg Ala Gly Val Ser Arg Ala Ala Leu Leu Arg Leu Phe Leu Ala
    290                 295                 300 atg cag aag ggc aag cat atg gaa ctt gac tgt cca tac ctg gtt cat              960
Met Gln Lys Gly Lys His Met Glu Leu Asp Cys Pro Tyr Leu Val His
305                 310                 315                 320 gtg ccc gtg gtt gct ttc cgc ctg gag ccc agg agc cag agg ggc gtg             1008
Val Pro Val Val Ala Phe Arg Leu Glu Pro Arg Ser Gln Arg Gly Val
                325                 330                 335 ttt tct gtg gat gga ggg ctg atg gta tgt gaa gct gtg cag ggc caa             1056
Phe Ser Val Asp Gly Gly Leu Met Val Cys Glu Ala Val Gln Gly Gln
            340                 345                 350 gtg cac cca aac tac ctt tgg atg gtc tgt ggc agc aga gat gcc cca             1104
Val His Pro Asn Tyr Leu Trp Met Val Cys Gly Ser Arg Asp Ala Pro
        355                 360                 365 tcc ggc cgg gac tcc cgg cgg ggg cca cct cca gaa gaa cca taa                 1149
Ser Gly Arg Asp Ser Arg Arg Gly Pro Pro Pro Glu Glu Pro
    370                 375                 380

SEQ ID NO 6

<211> LENGTH: 382
```

```
<212> TYPE: PRT
<213> ORGANISM: Mus musculus

<400> SEQUENCE: 6

Met Glu Pro Val Glu Cys Pro Arg Gly Leu Leu Pro Arg Pro Cys Arg
1               5                   10                  15

Val Leu Val Leu Leu Asn Pro Gln Gly Lys Gly Lys Ala Leu Gln
            20                  25                  30

Leu Phe Gln Ser Arg Val Gln Pro Phe Leu Glu Glu Ala Glu Ile Thr
        35                  40                  45

Phe Lys Leu Ile Leu Thr Glu Arg Lys Asn His Ala Arg Glu Leu Val
    50                  55                  60

Cys Ala Glu Glu Leu Gly His Trp Asp Ala Leu Ala Val Met Ser Gly
65                  70                  75                  80

Asp Gly Leu Met His Glu Val Val Asn Gly Leu Met Glu Arg Pro Asp
                85                  90                  95

Trp Glu Thr Ala Ile Gln Lys Pro Leu Cys Ser Leu Pro Gly Gly Ser
            100                 105                 110

Gly Asn Ala Leu Ala Ala Ser Val Asn His Tyr Ala Gly Tyr Glu Gln
        115                 120                 125

Val Thr Asn Glu Asp Leu Leu Ile Asn Cys Thr Leu Leu Leu Cys Arg
    130                 135                 140

Arg Arg Leu Ser Pro Met Asn Leu Leu Ser Leu His Thr Ala Ser Gly
145                 150                 155                 160

Leu Arg Leu Tyr Ser Val Leu Ser Leu Ser Trp Gly Phe Val Ala Asp
                165                 170                 175

Val Asp Leu Glu Ser Glu Lys Tyr Arg Arg Leu Gly Glu Ile Arg Phe
            180                 185                 190

Thr Val Gly Thr Phe Phe Arg Leu Ala Ser Leu Arg Ile Tyr Gln Gly
        195                 200                 205

Gln Leu Ala Tyr Leu Pro Val Gly Thr Val Ala Ser Lys Arg Pro Ala
    210                 215                 220

Ser Thr Leu Val Gln Lys Gly Pro Val Asp Thr His Leu Val Pro Leu
225                 230                 235                 240

Glu Glu Pro Val Pro Ser His Trp Thr Val Pro Glu Gln Asp Phe
                245                 250                 255

Val Leu Val Leu Val Leu Leu His Thr His Leu Ser Ser Glu Leu Phe
            260                 265                 270

Ala Ala Pro Met Gly Arg Cys Glu Ala Gly Val Met His Leu Phe Tyr
        275                 280                 285

Val Arg Ala Gly Val Ser Arg Ala Ala Leu Leu Arg Leu Phe Leu Ala
    290                 295                 300

Met Gln Lys Gly Lys His Met Glu Leu Asp Cys Pro Tyr Leu Val His
305                 310                 315                 320

Val Pro Val Val Ala Phe Arg Leu Glu Pro Arg Ser Gln Arg Gly Val
                325                 330                 335

Phe Ser Val Asp Gly Gly Leu Met Val Cys Glu Ala Val Gln Gly Gln
            340                 345                 350

Val His Pro Asn Tyr Leu Trp Met Val Cys Gly Ser Arg Asp Ala Pro
        355                 360                 365

Ser Gly Arg Asp Ser Arg Arg Gly Pro Pro Glu Glu Pro
370                 375                 380
```

INDUCTION OF BLOOD VESSEL FORMATION THROUGH ADMINISTRATION OF POLYNUCLEOTIDES ENCODING SPHINGOSINE KINASES

This application claims the benefit under 35 USC §119(e) of the following United States provisional patent application: Provisional Application No. 60/238,230, filed on Oct. 5, 2000, for "Induction of Blood Vessel Formation Through Administration of Polynucleotides Encoding Sphingosine Kinases." The disclosure of that application is incorporated hereby by reference in its entirety.

This invention relates to the induction of blood vessel formation. More particularly, this invention relates to the induction of blood vessel formation in an animal by administering to the animal a sphingosine kinase, or an analogue, fragment, or derivative thereof. Preferably, the sphingosine kinase, or analogue, fragment, or derivative thereof is administered by administering to the animal a polynucleotide encoding a sphingosine kinase, or an analogue, fragment, or derivative thereof. The polynucleotide encoding the sphingosine kinase may be contained in an appropriate expression vehicle or expression vector, such as an adenoviral vector.

BACKGROUND OF THE INVENTION

Vascular endothelial cells undergo morphogenesis into capillary networks in response to angiogenic factors. It was shown previously that sphingosine-1-phosphate, or SPP, a platelet-derived bioactive lipid, is an important sphingolipid-derived second messenger in mammalian cells that acts to promote proliferation and to inhibit apoptosis. (Olivera, et al., *Nature,* Vol. 365, pgs. 557–560 (Oct. 7, 1993); Spiegel, et al., *J. Leukoc. Biol.,* Vol. 65, No. 3, pgs. 341–344 (March 1999).) Recently, SPP was defined as a novel regulator of angiogenesis. (Lee, et al., *Cell,* Vol. 99, No. 3, pgs. 301–312 (Oct. 29, 1999).) SPP activates the endothelial cell differentiation genes (EDG) EDG-1 and EDG-3 subtypes of G protein-coupled receptors on endothelial cells. Both EDG-1 and EDG-3 regulated signaling pathways are required for endothelial cell morphogenesis into capillary-like networks. SPP induces the Gi/mitogen-activated protein kinase cell survival pathway and enhances small GTPase Rho and Rac coupled adherens junction assembly. (Lee, 1999.) The level of SPP is regulated potentially by the enzyme that catalyzes the phosporylation of sphingosine to SPP. The cloning and characterization of the first mammalian sphingosine kinases (murine SPHK1α and SPHK1β) has been reported. (Kohama, et al., *J. Biol. Chem.,* Vol. 273, No. 37, pgs. 23722–23728 (Sep. 11, 1998)). Human sphingosine kinases (SPHK1 and SPHK2) have also been reported. (Nava, et al., *FEBS,* 473:81–84 (2000) and Liu, et al., J. Biol. Chem., 275:19513–19520 (2000).)

SUMMARY OF THE INVENTION

Applicants have discovered that the administration of sphingosine kinase, and in particular, that vector-mediated expression of sphingosine kinase enhances the formation of new blood vessels. Thus, the present invention is directed to inducing blood vessel formation in an animal by administering to the animal a sphingosine kinase, preferably by administering to the animal a polynucleotide encoding a sphingosine kinase or an analogue, fragment, or derivative thereof. The sphingosine kinase, or analogue, fragment, or derivative thereof, or polynucleotide encoding sphingosine kinase or an analogue, fragment, or derivative thereof, may be administered in combination with other angiogenic proteins or polynucleotides encoding other angiogenic proteins such as, but not limited to, VEGF, FGF, IGF, angiopoietins, PD-EGF, TGFβ, HIF1-α, nitric oxide synthase, MCP-1, Interleukin-8, ephrins, NAP-2, ENA-78, GROW-2, and fragments of tyrosyl-tRNA synthetase that have angiogenic activity as disclosed in U.S. patent applications Ser. Nos. 60/193,471 filed Mar. 31, 2000, and 09/813,718, filed Mar. 21, 2001. The polynucleotide encoding the sphingosine kinase may be contained in an appropriate expression vehicle or expression vector, such as a viral vector. The administration of a polynucleotide encoding a sphingosine kinase to an animal is a method by which SPP can be delivered at elevated levels to a local site, and such method provides for the formation of larger vessels containing a well-defined structure that is supported by mural cells such as pericytes and smooth-muscle cells.

BRIEF DESCRIPTION OF THE DRAWINGS

The invention now will be described with respect to the drawings, wherein:

FIG. 2 shows the cDNA and amino acid sequences for murine sphingosine kinase 1α.

FIG. 5A shows a hematoxylin and eosin stained section of matrigel treated with S8 cells transduced with an adenoviral vector expressing sphingosine kinase. FIG. 5B is the same section stained with α-smooth muscle (α-SM) actin. FIG. 5C is a section of a matrigel plug treated with FGF generated capillaries.

DETAILED DESCRIPTION OF THE INVENTION

Figure 1:
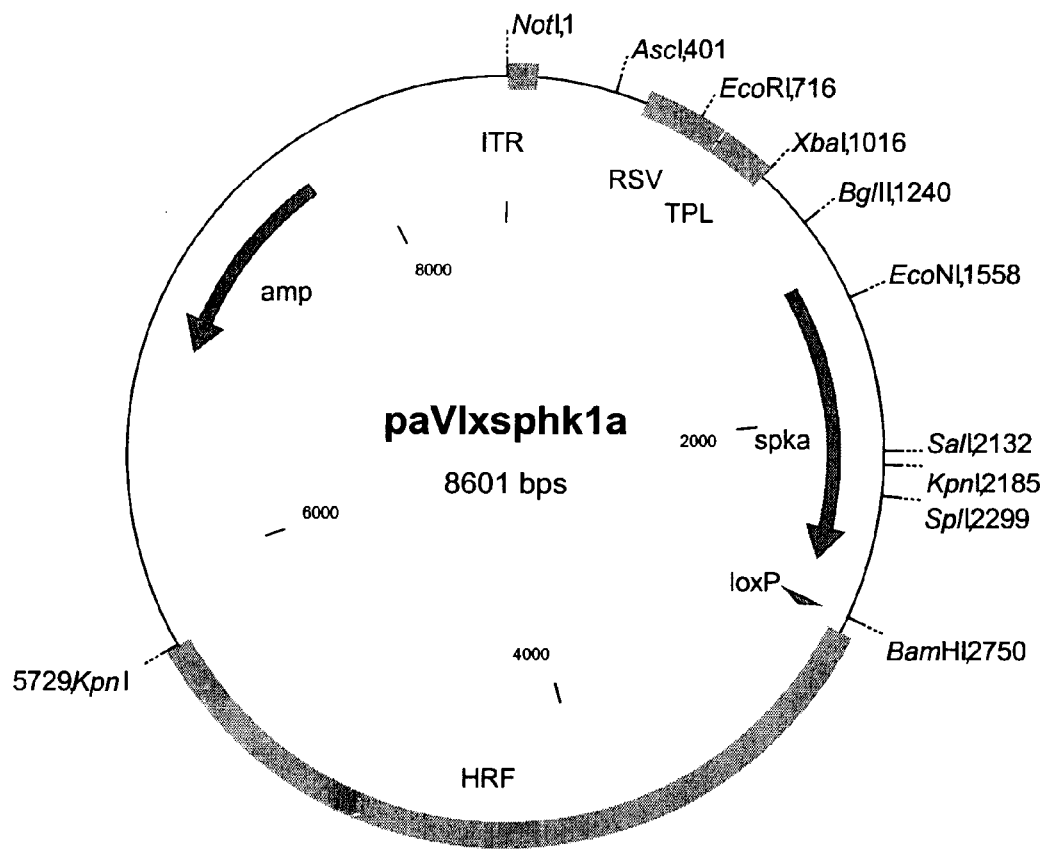
FIG. 1 is a map of the plasmid pAv1xsphK1α.

In accordance with an aspect of the present invention, there is provided a method of inducing blood vessel formation in an animal. The method comprises administering to the animal an effective amount of a sphingosine kinase or an analogue, fragment, or derivative thereof.

In accordance with another aspect of the present invention, there is provided a method for the prevention or the treatment of congestive heart failure in an animal. The method comprises administering to said an effective amount of animal a sphingosine kinase, or an analogue, fragment, or derivative thereof.

In accordance with yet another aspect of the present invention, there is provided a method for the prevention or the treatment of myocardial ischemia in an animal. The method comprises administering to said animal an effective amount of a sphingosine kinase, or an analogue, fragment, or derivative thereof.

In accordance with yet another aspect of the present invention, there is provided a method for the prevention or the treatment of ischemia-reperfusion injury in an animal. The method comprises administering to said animal an effective amount of a sphingosine kinase, or an analogue, fragment, or derivative thereof.

In a preferred embodiment, the sphingosine kinase, or analogue, fragment, or derivative thereof is administered to the animal by administering to the animal an effective amount of a polynucleotide encoding a sphingosine kinase, or an analogue, fragment, or derivative thereof. The sphingosine kinase is mammalian, preferably primate, and most preferably human sphingosine kinase. Specific examples of sphingosine kinase amino acid sequences and the polynucleotides encoding them are found in Genbank for human SPHK1 and SPHK2 (accession numbers AF200328 and AF245447), mouse SPHK1α, SPHK1β, and SPHK2 (accession numbers AF068748, AF068749, and AF245448), and rat SPHK1a, SPHK1c, SPHK1d, SPHK1e, and SPHK1f (accession numbers AB049571, AB049572, AB049573, AB049574, and AB049575). SEQ. ID NO:1 and SEQ ID NO:2 show the cDNA and amino acid sequences for human SPHK1. SEQ ID NO:3 and SEQ ID NO:4 show the cDNA and amino acid sequences for human SPHK2. An analogue of sphingosine kinase includes, but is not limited to, splice variants of sphingosine kinase, deletions in the coding region, and multiple forms (T. Kohama et al., JBC, 273:23722–23728 (1998); H. Liu et al., JBC, 275:19513–19520 (2000); Y. Banno, et al., Biochem J., 335:301–304 (1998)). A fragment of sphingosine kinase is a portion of the protein that retains its activity for inducing blood vessel formation. A derivative of sphingosine kinase includes, but is not limited to, modifications to alter sphingosine kinase regulation or biological activity. Non-limiting examples include the addition of a signal sequence to force secretion of the enzyme or modification of the calcium, calmodulin binding domain, ATP binding site, or membrane retention sequences. The polynucleotide is under the control of a suitable promoter. It is to be understood, however, that the scope of the present invention is not to be limited to any specific promoters.

Preferably, the polynucleotide encoding the sphingosine kinase, or an analogue, fragment, or derivative thereof is contained in an appropriate expression vehicle. Such expression vehicles include, but are not limited to, plasmids, eukaryotic vectors, prokaryotic vectors (such as, for example, bacterial vectors), and viral vectors. In one embodiment, the vector is a viral vector. Viral vectors which may be employed include RNA virus vectors (such as retroviral vectors, including lentiviral vectors) and DNA virus vectors (such as adenoviral vectors, adeno-associated virus vectors, Herpes Virus vectors, and vaccinia virus vectors). When a DNA virus vector is employed in constructing the vector, the polynucleotide encoding the sphingosine kinase is in the form of DNA. When an RNA virus vector is employed in constructing the vector, the polynucleotide encoding the sphingosine kinase is in the form of RNA. Preferable viral vectors include adenoviral vectors (preferably lacking all viral genes, i.e. high capacity or gutless), lentiviral vectors (e.g. HIV, BIV-based), and adeno-associated virus (AAV) vectors.

In one embodiment, the viral vector including the polynucleotide encoding sphingosine kinase, or an analogue, fragment, or derivative thereof is an adenoviral vector.

The adenoviral vector which is employed may, in one embodiment, be an adenoviral vector which includes essentially the complete adenoviral genome (Shenk et al., Curr. Top. Microbiol. Immunol., 111(3): 1–39 (1984). Alternatively, the adenoviral vector may be a modified adenoviral vector in which at least a portion of the adenoviral genome has been deleted.

In a preferred embodiment, the adenoviral vector comprises an adenoviral 5' ITR; an adenoviral 3' ITR; an adenoviral encapsidation signal; a DNA sequence encoding a sphingosine kinase, or an analogue, fragment, or derivative thereof, and a promoter controlling the DNA sequence encoding a sphingosine kinase, or an analogous, fragment, or derivative thereof. The vector is free of at least the majority of adenoviral E1 and E3 DNA sequences, but is not free of all of the E2 and E4 DNA sequences, and DNA sequences encoding adenoviral proteins promoted by the adenoviral major late promoter. In one embodiment, the vector also is free of at least a portion of at least one DNA sequence selected from the group consisting of the E2 and E4 DNA sequences.

In another embodiment, the vector is free of at least the majority of the adenoviral E1 and E3 DNA sequences, and is free of a portion of the other of the E2 and E4 DNA sequences.

In still another embodiment, the gene in the E2a region that encodes the 72 kilodalton binding protein is mutated to produce a temperature sensitive protein that is active at 32° C., the temperature at which the viral particles are produced. This temperature sensitive mutant is described in Ensinger, et al., J. Virology, 10:328–339 (1972), Van der Vliet et al., J. Virology, 15:348–354 (1975), and Friefeld, et al., Virology, 124:380–389 (1983).

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a multiple cloning site (which may be as herein described); a poly A signal; and a DNA segment which corresponds to a segment of the adenoviral genome. The promoter may, in one embodiment, be a regulatable promoter, such as, for example, a glucocorticoid-responsive promoter or an estrogen-responsive promoter, or the promoter may be a tissue—specific promoter. The vector also may, in another embodiment, contain genomic elements which may increase and/or maintain expression of the DNA sequence encoding a sphingosine kinase, or an analogue, fragment, or derivative thereof. Such genomic elements include, but are not limited to, introns, exons, polyadenylation sequences, and 5' and 3' untranslated regions. Such genomic elements, and representative examples thereof, also are described in U.S. Pat. No. 5,935,935, issued Aug. 10, 1999. The vector also may contain a tripartite leader sequence. The DNA segment which corresponds to a segment of the adenoviral genome serves as a substrate for homologous recombination with an adenovirus. The plasmid may also include a selectable marker and an origin of replication. The origin of replication may be a bacterial origin of replication. Representative examples of such shuttle plasmids include pAvS6, which is described in published PCT Application Nos. WO 94/23582, published Oct. 27, 1994, and WO 95/09654, published Apr. 13, 1995, and in U.S. Pat. No. 5,543,328, issued Aug. 6, 1996. The DNA sequence encoding a sphingosine kinase, or an analogue, fragment, or derivative thereof then may be inserted into the multiple cloning site of the shuttle plasmid to produce a plasmid vector.

This construct is then used to produce an adenoviral vector. Homologous recombination may be effected through co-transfection of the plasmid vector and the adenovirus into a helper cell line, such as 293 cells, by $CaPO_4$ precipitation. Upon such homologous recombination, a recombinant adenoviral vector is formed that includes DNA sequences derived from the shuttle plasmid between the 5'ITR and the homologous recombination fragment, and the DNA derived from the adenovirus between the homologous recombination fragment and the 3' ITR.

In one embodiment, the homologous recombination fragment overlaps with nucleotides 3329 to 6246 of the Adenovirus 5 (ATCC VR-5) genome.

Through such homologous recombination, a vector is formed which includes an adenoviral 5' ITR, an adenoviral encapsidation signal; an E1a enhancer sequence; a promoter; a DNA sequence encoding a sphingosine kinase, or an analogue, fragment, or derivative thereof; a poly A signal; adenoviral DNA sequences; and an adenoviral 3' ITR. The vector also may include a tripartite leader sequence. The vector may then be transfected into a helper cell line, such as the 293 helper cell line (ATCC No. CRL1573), which will include the E1a and the E1b DNA sequences, which are necessary for viral replication, and to generate adenoviral particles. Transfection may take place by electroporation, calcium phosphate precipitation, microinjection, or through proteoliposomes.

In another embodiment, the adenoviral vector is free of all or a portion of each of the adenoviral E1 and E4 DNA sequences, or is free of all or a portion of each of the adenoviral E1 and E2 DNA sequences, or is free of all or a portion of each of the E1, E2, and E4 DNA sequences.

Such vectors may be assembled by direct in vitro ligation from combinations of plasmids containing portions of modified or unmodified virus genome or plasmids and fragments derived directly from a linear adenoviral genome, such as the Adenovirus 5 genome (ATCC No. VR-5) or Adenovirus 5 derived viruses containing mutations or deletions.

In another alternative, the vectors can be assembled by homologous recombination, within a eukaryotic cell, between a plasmid clone containing a portion of the adenoviral genome (such as the Adenovirus 5 genome or the adenovirus 5 E3-mutant Add1327 (Thimmapaya, et al., Cell, Vol. 31, pg, 543 (1983)) with the desired modifications, and a second plasmid (such as, for example pAvS6), containing the left adenoviral ITR, an E1 region deletion, and the desired transgene. Alternatively, homologous recombination may be carried out between a plasmid clone and a fragment derived directly from a linear adenovirus (such as Adenovirus 5, or Ad d1327 or an Adenovirus 5 derived virus containing mutations or deletions) genome.

The vector then is transfected into a cell line capable of complementing the function of any essential genes deleted from the viral vector, in order to generate infectious viral particles. The cell line in general is a cell line, which is infectable and able to support adenovirus or adenoviral vector growth and provide for continued virus production. Cell lines which may be transfected with the essential adenoviral genes, and thus may be employed for generating the infectious adenoviral particles include, but are not limited to, the A549, KB, and Hep-2 cell lines.

Because the expression of some viral genes may be toxic to cells, the E1 region, as well as the E2b, and/or E4 regions, may be under the control of an inducible promoter. Such inducible promoters may include, but are not limited to, the mouse mammary tumor virus (MMTV) promoter (Archer, et al., Science, Vol. 255, pgs. 1573–1576 (Mar. 20, 1992)); the synthetic minimal glucocorticoid response element promoter GRE5 (Mader, et al., Proc. Nat. Acad. Sci., Vol. 90, pgs. 5603–5607 (June 1993)); or the tetracycline-responsive promoters (Gossen, et al., Proc. Nat. Acad. Sci., Vol. 89, pgs. 5547–5551 (June 1992)). In another alternative, the E1 region is under the control of an inducible promoter, and the E2a, E2b and/or E4 regions are under the control of their native promoters. In such alternative, the native promoters are transactivated by expression of the E1 region.

In one embodiment, the cell line includes the entire adenoviral E4 region with its native promoter region, and the Ela region or the entire E1 region (including the E1a and E1b regions) under the control of a regulatable or inducible promoter, such as, for example, the mouse mammary tumor virus (or MMTV) promoter, which is a hormone inducible promoter, or other such promoters containing glucocorticoid responsive elements (GRE's) for transcriptional control. In another embodiment, the E4 DNA sequence also is expressed from a regulatable promoter, such as the MMTV promoter. The E1 and E4 DNA sequences may be included in one expression vehicle, or may be included in separate expression vehicles. Preferably, the expression vehicles are plasmid vectors which integrate into the genome of the cell line.

Such vectors, wherein the vector is free of all or a portion of each of the adenoviral E1 and E4 DNA sequences, or is free of all or a portion of each of the adenoviral E1 and E2 DNA sequences, or is free of all or a portion of the E1, E2 and E4 DNA sequences, and the complementing cell lines, also are described in PCT Application No. WO96/18418, published Jun. 20, 1996, the contents of which are incorporated herein by reference.

In another embodiment, the adenoviral vector is free of all adenoviral coding regions. This "gutless" adenoviral vector includes an adenoviral 5' ITR, an adenoviral packaging signal, a DNA sequence encoding sphingosine kinase or an analogue, fragment, or derivative thereof, and an adenoviral 3' ITR. The vector contains from about 26 kb to about 38 kb, preferably 28 kb to 32 kb, and may include one or more genomic elements.

The various adenoviral vectors may include promoters other than a sphingosine kinase promoter, such as tissue-specific promoters. The vector also may include, in addition to a DNA sequence encoding a sphingosine kinase, or an analogue, fragment, or derivative thereof, DNA sequences encoding additional proteins which facilitate the generation of new blood vessels, such as, but not limited to, vascular endothelial growth factors (VEGFs), fibroblast growth factors (FGFs), IGFs, angiopoietins, including angiopoietin 1, and angiopoietin 2, TGF-β, hypoxia inducible factors (HIFs) such as HIF1-α, monocyte chemoattractant proteins (MCPs) such as MCP-1, nitric oxide synthase, ephrins, such as ephrin B2, and other angiogenic genes, platelet derived endothelial growth factor, and Interleukin-8.

The adenoviral vector of the present invention may be administered to a host in vivo in an amount effective to promote blood vessel formation in an animal host. The host may be a mammalian host, including human and non-human primate hosts.

In one embodiment, the adenoviral vector is administered in an amount from about $10^7$ plaque forming units to about $10^{12}$ plaque forming units, preferably from about $5 \times 10^8$ plaque forming units to about $2 \times 10^{11}$ plaque forming units. Alternatively, cells transduced with the adenoviral vector may be administered in an amount of from about $10^3$ to $10^8$ cells.

In general, the adenoviral vectors are administered at the local site of ischemia or where therapeutic angiogenesis is required. Delivery can be performed by a variety of means including, but not limited to, direct injection of the adenoviral vector or cells transduced with the adenoviral vector, intraarterial delivery by a guided catheter or by computer guided systems such as NOGA, or by electroporation.

Alternatively, the adenoviral vector may have a modified fiber protein whereby the adenoviral vector is "targeted" to a specific cell. Representative examples of such adenoviral vectors are disclosed in U.S. Pat. No. 5,543,328. Such adenoviral vectors may be administered systemically, such as by intravenous administration (such as, for example, portal vein injection or peripheral vein injection), or intraarterial administration, including hepatic artery administration.

The adenoviral vectors may be administered in combination with a pharmaceutically acceptable carrier suitable for administration to a patient. The carrier may be a liquid carrier (for example, a saline solution), or a solid carrier, such as, for example, microcarrier beads or localizing agents such as calcitonin gel, hyaluronan solutions, or fibrin plugs derived from the activation of fibrinogen by thrombin (U.S. Pat. No. 6,117,425).

In one embodiment, the viral vector is a retroviral vector. Retroviral vectors, including lentiviral viral vectors, have a coding capacity of approximately 8 kb, and the viral genome is capable of integration into the host cell chromosome, thus allowing for potentially life-long transgene expression. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, myeloproliferative sarcoma virus, and mammary tumor virus, as well as lentiviral vectors. One non-limiting example of a lentivirus is Bovine-Immunodeficiency-Virus (BIV). See PCT patent publication WO 01/44458. The vector generally is a replication incompetent retrovirus particle.

In one embodiment, the retroviral vector may be generated from a retroviral plasmid vector which is derived from Moloney Murine Leukemia Virus and is of the LN series of vectors, which are described further in Bender, et al., *J. Virol.*, Vol. 61, pgs. 1639–1649 (1987) and Miller, et al., *Biotechniques*, Vol. 7, pgs 980–990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral plasmid vector may include at least one cloning, or restriction enzyme recognition site, wherein the site(s) has an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral plasmid vector includes each of these cloning sites. Such vectors are further described in U.S. Pat. No. 5,672,510.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral plasmid vector. The shuttle cloning vector also includes a polynucleotide encoding a sphingosine kinase, or an analogue, fragment or derivative thereof which is capable of being transferred from the shuttle cloning vector to the retroviral plasmid vector.

In one embodiment the viral vector is a lentiviral vector, for example derived from BIV. Lentiviral vectors are generally constructed such that the majority of the viral genes are deleted and replaced by a gene of interest. Most frequently the gene of interest is transcribed under the control of the viral regulatory sequences within the long terminal repeat (LTR). Alternatively, the gene of interest may be expressed under the regulation of an internal promoter. The genes which have been deleted from the vector are generally provided by one or more helper or packaging constructs in a packaging cell line (Bender et al., J. Virol. 61:1639–1649 (1987) and Miller et al., Biotechniques, 7:980–990 (1989)). Also see Markowitz et al., J. Virol. 62:1120–1124 (1988) wherein complementary portions of the helper construct were divided on two separate constructs. The packaging cell line may be transfected with the retroviral vector, thereby producing vector RNA that is packaged into the virus particles. These released virus particles are replication defective and can be used to deliver the retroviral vector carrying the gene of interest to target cells.

To increase safety, efficiency and accuracy of the recombinant vector systems, various improved recombinant systems have been constructed. One type of improvement includes making safer packaging cell lines that are generated by deletions in the 3' Long Terminal Repeat (LTR). Other improvements include increasing the host range by replacement of one viral env gene with that of another viral env gene thereby creating a hybrid producer line that generates pseudotyped helper viruses. More specifically HIV has been given an extended host cell range by pseudotyping with the unrelated viruses VSV and HSV (Zhu et al., J. Aids, 3:215–219 (1990) and Naldini et al., Science, 272:263–267, (1996)). Further improvements have been made by the use of minimum viral coding regions on the vector. Lentivirus can infect nondividing cells, and this property is especially useful for in vivo gene therapy. Additionally, most packaging cell lines currently in use have been transfected with separate plasmids, each containing one of the necessary coding sequences so that multiple recombination events would be necessary before replication competent virus can be produced. U.S. Pat. Nos. 5,665,577, 5,994,136, 6,013,516 describes examples of lentiviral vector systems. U.S. patent application Ser. No. 09/734,836 and PCT patent publication WO 01/44458 describe examples of BIV based lentiviral vector systems.

In one embodiment, an effective amount of the lentiviral vector is administered to an animal in an amount from about $5 \times 10^5$ transducing units to about $10^{12}$ transducing units. In a preferred embodiment, the effective amount delivered to the animal is from about $5 \times 10^5$ transducing units to about $10^{10}$ transducing units.

In one embodiment, in addition to the polynucleotide encoding sphingosine kinase or an analogue, fragment, or derivative thereof, the retroviral plasmid vector also may include polynucleotides encoding additional proteins which facilitate the generation of new blood vessels, such as, but not limited to, insulin like growth factor (IGF), angiopoietins, including angiopoietin1 and angiopoietin2, FGF, nitric oxide synthase, Interleukin-8, and TGF-β.

The shuttle cloning vector may be constructed from a basic "backbone" vector or fragment to which are ligated one or more linkers which include cloning or restriction enzyme recognition sites. Included in the cloning sites are the compatible, or complementary cloning sites herein above described. A polynucleotide encoding a sphingosine kinase, or an analogue, fragment, or derivative thereof and/or a promoter having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector may include a promoter for expressing a polynucleotide encoding a sphingosine kinase, or an analogue, fragment, or derivative thereof. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, cyclin G1, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The retroviral plasmid vector including the polynucleotide encoding a sphingosine kinase, or an analogue, fragment, or derivative thereof is transduced into a packaging cell line including nucleic acid sequences encoding the gag, pol, and env retroviral proteins. Examples of such packaging cell lines include, but are not limited to, the PE501, PA317 (ATCC No. CRL 9078), Ψ-2, Ψ-AM, PA12, T19-14X, VT-19-17-H2, ΨCRE, ΨCRIP, GP+E-86, GP+envAm12, and DAN cell lines as described in Miller, *Human Gene Therapy*, Vol. 1, pgs. 5–14 (1990), which is incorporated herein by reference in its entirety, or the 293T cell line (U.S. Pat. No, 5,952,225). The vector may transduce the packaging cells through any means known in the art. Such means include, but are not limited to, electroporation, the use of liposomes, and $CaPO_4$ precipitation. Such producer cells generate infectious retroviral vector particles which include the polynucleotide encoding a sphingosine kinase, or an analogue, fragment, or derivative thereof.

The retroviral vector particles or cells transduced with a retroviral vector are administered to an animal in an amount which is effective to promote blood vessel formation. Administration of the retroviral vector particles may be by local administration, such as direct injection of the vectors or cells transduced with the vectors, intraarterial delivery by a guided catheter, by computer guided systems such as NOGA and by electroporation. In general, the retroviral vectors are administered in an amount of at least $10^4$ cfu/ml, and in general, such an amount does not exceed $10^9$ cfu/ml. The exact dosage to be administered is dependent upon a variety of factors including the age, weight, and sex of the animal or patient to be treated, and the disease or disorder being treated.

The retroviral vectors also may be administered in conjunction with an acceptable pharmaceutical carrier, such as, for example, saline solution, protamine sulfate (Elkins-Sinn, Inc., Cherry Hill, N.J.), water, aqueous buffers, such as phosphate buffers and Tris buffers, or Polybrene (Sigma Chemical, St. Louis, Mo.), or localizing agents such as calcitonin gel, hyaluronan solutions, or fibrin plugs derived from the activation of fibrinogen by thrombin (U.S. Pat. No. 6,117,425). The selection of a suitable pharmaceutical carrier is deemed to be apparent to those skilled in the art from the teachings contained herein.

In another alternative, the retroviral vectors hereinabove described, or a polynucleotide encoding a sphingosine kinase, or an analogue, fragment, or derivative thereof, may be encapsulated within liposomes. The liposomes, which encapsulate the retroviral vectors or a polynucleotide encoding sphingosine kinase, or analogue, fragment, or derivative thereof, may be administered to a host in conjunction with a pharmaceutical carrier as hereinabove described.

In another alternative, retroviral producer cells, such as those derived from the packaging cell lines herein above described, which include a polynucleotide encoding a sphingosine kinase, or an analogue, fragment, or derivative thereof, may be administered to an animal. Such producer cells may, in one embodiment, be administered systemically (e.g., intravenously or intraarterially). The producer cell line then produces retroviral vectors including a polynucleotide comprising the polynucleotide encoding a sphingosine kinase, or an analogue, fragment, or derivative thereof.

Another embodiment has the expression of sphingosine kinase controlled by an inducible promoter. The use of an inducible gene expression system would allow the precise regulation of sphingosine kinase in a reversible manner. Several inducible systems are currently available. One example of a controlled promoter system in the Tet-On™ and Tet-Off™ systems currently available from Clontech (Palo Alto, Calif.). Tet-Off™ system uses the tetracycline-controlled transactivator (tTA), which is composed of the tet repressor protein (TetR) and the VP16 activation domain. tTA activates transcription in the absence of tetracycline. The Tet-On™ system uses the reverse tetracycline-controlled transactivator (rtTA) and activates transcription in the presence of tetracycline. Both systems use the tetracycline-response element (TRE), which contains 7 repeats of the tet operator sequence, and the target gene, such as sphingosine kinase. tTA or rtTA bind to the TRE, activating transcription of the target gene. This promoter system allows the regulated expression of the transgene controlled by tetracycline or tetracycline derivatives, such as doxycycline. This system could be used to control the expression of sphingosine kinase in this instant invention.

Other regulatable promoter systems are described in the U.S. patent applications Ser. No. 09/586,625 and provisional application, number to be assigned, filed Jul. 18, 2000, as application Ser. No. 09/619,063 for "Regulation of Gene Expression Using Single-Chain, Monomeric, Ligand Dependent Polypeptide Switches" and subject to a petition for conversion to provisional application, filed Jul. 18, 2001.

The expression vehicles, such as adenoviral vectors or retroviral vectors (including lentiviral vectors), or cells transduced with such expression vehicles, may be employed in the treatment of a variety of diseases or disorders. Such diseases and disorders include, but are not limited to, coronary artery disease, peripheral vascular disease, wound healing and fracture repair, reconstructive surgery, transplantation such as islet transplants, tendon repair/sports injury, healing of ulcers, thromboangitis obliterans (Buerger's disease), periodontal tissue regeneration, and radiotherapy-induced esophagitis.

Contractile function loss in the heart is a major disease indication with 15 million worldwide and around 500,000 per year diagnosed with congestive heart failure (Massie, B. and Shah, N. *American Heart Journal*, 1997; 133:703–712).

Congestive heart failure may be caused by myocardial ischemia and can be treated by therapeutic angiogenesis. Therapeutic angiogenesis can also replace current surgical interventions for the treatment of myocardial ischemia including percutaneous coronary intervention and coronary arterial bypass surgery. In addition, critical limb ischemia which develops in 500–1,000 people per million per year, often is not amenable to surgical or percutaneous revascularization and results in the loss of the limb. Again therapeutic angiogenesis can be used to treat this disease. A particular form of this disease is thromboangitis obliterans or Buerger's disease and preliminary clinical studies suggest an angiogenic approach may provide a novel therapy for patients with this disease. Sphingosine kinase-mediated angiogenesis can also be used to accelerate wound healing which requires a robust angiogenic response in granulation tissues following insults such as burns and to stimulate angiogenesis for better repair of bone fracture, bone grafts, and in healing tendons. Other possible use of this treatment include ulcer healing, periodontal tissue regeneration, reconstructive surgery and radiotherapy-induced esophagitis. Transplantation of encapsulated pancreatic islets is a promising treatment of type 1 diabetes and can greatly benefit from the use of sphingosine kinase to enhance vascularization (de Vos et al., 1997).

For the treatment of congestive heart failure, myocardial ischemia, ischemia-reperfusion injury or peripheral arterial diseases, the lentiviral vector is administered to an animal in an effective amount from about $5 \times 10^5$ transducing units to about $10^{12}$ transducing units. In a preferred embodiment the effective amount delivered to the animal is from about $5 \times 10^5$ transducing units to about $10^{10}$ transducing units.

For the treatment of congestive heart failure, myocardial ischemia, ischemia-reperfusion injury or peripheral arterial diseases, the adenoviral vector is administered in an effective amount from about $10^7$ plaque forming units to about $10^{12}$ plaque forming units, preferably from about $5 \times 10^8$ plaque forming units to about $2 \times 10^{11}$ plaque forming units. Alternatively, cells transduced with the adenoviral vector may be administered in an amount of from about $10^3$ to $10^8$ cells.

EXAMPLES

The invention now will be described with respect to the following examples; however, the scope of the present invention is not intended to be limited thereby.

Example 1
Sphingosine Kinase Cloning and Southern Analysis

The plasmid pCR3.1sphK1α, derived from pCR3.1 (Invitrogen), was obtained from Thomas Baumruker (Novartis, Vienna, Austria) and contains the mouse sphingosine kinase alpha cDNA. pCR3.1sphK1x was digested with HindIII and NotI to isolate a 1,531 bp insert containing the coding sequence for sphK1α. The fragment was blunt-ended and cloned into the EcoRV site of pAVS6a1x, an adenoviral shuttle plasmid containing a lox recombination site, to create pAV1xsphK1α (FIG. 1). pAVS6a1x had been formed by adding a lox site to pAVS6a (U.S. Pat. No. 5,543,328). A 535 bp ClaI/NcoI fragment from pAVH8–1011x, containing the SV40 polyA signal and lox site was inserted into pAVS6a digested with ClaI and NcoI and linearized (4,745 bp). The sphK1α cDNA was cloned downstream of the RSV promoter and the adenoviral tripartite leader sequence, and included the SV40 polyadenylation signal and a homologous recombination region. A large-scale plasmid preparation was prepared using the alkaline lysis method and purified using a CsTFA gradient following standard protocols. The cDNA then was sequenced. The sphK1α coding sequence is 1,149 bp (SEQ ID NO:5) and encodes a 382 amino acid protein (SEQ ID NO:6). The cDNA and amino acid sequences are shown in FIG. 2.

Generation of a Recombinant Adenoviral Vector

Figure 3:
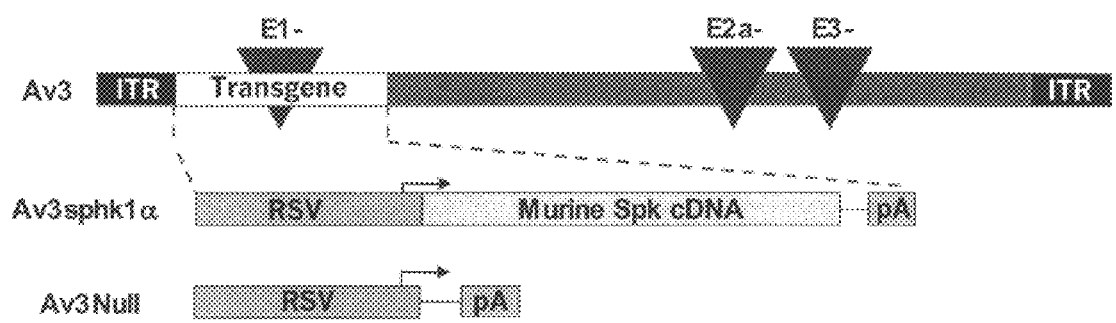
FIG. 3 is a schematic of the adenoviral vector Av3sphK1α.

The sphk1α cDNA was incorporated into an adenoviral vector using the lox recombination three-plasmid transfection system. AE1-2a cells (Gorziglia et al., *J. Virol.*, Vol. 70, No. 6, pgs. 4173-4178 (1996)), also known as S8 cells, were cultured in Richters media containing 5% heat inactivated fetal bovine serum (FBS). Transient transfections of the AE1-2a cells were performed with 0.5 μg of Not1-digested pAv1xsphk1α, 0.5 ug of pCcre and 1 μg of ClaI-digested pSQ3 DNA using the LipofectAMINE-PLUS reagent system (Life Technologies, Rockville, Md.). Plasmid pSQ3 is a 31,574 bp plasmid containing adenoviral structural genes, but is devoid of E1, E2a, and E3 sequences. S8 cells were incubated with the lipofectamine reagent/DNA precipitate at 37° C. for 16 hours. The precipitate was removed and the monolayers were washed with PBS. Richters media containing 5% FBS and 0.3 uM dexamethasone was added to the cells. The cells were incubated at 37° C. for approximately 5–7 days. At that time the conditioned media and cells were collected, frozen and thawed three times and the cell debris was pelleted. The conditioned media was then used to infect a fresh plate of dexamethasone-induced S8 cells. A cytopathic effect was observed in the cells approximately 12–15 days post-transfection. The virus was amplified in 15 cm dishes of dexamethasone-induced S8 cells. The recombinant Av3sphk1α vector (FIG. 3) was purified and a large scale preparation seedlot was prepared.

Southern Blot Analysis

The genomic organization and purity of Av3sphk1α was verified by DNA analysis of isolated viral DNA by restriction endonuclease digestion and Southern blot analysis following standard protocols using a [$^{32}$P]-labeled sphk1α cDNA probe. DNA was isolated from Av3nBg, described in published PCT Application No. WO96/18418, and Av3sphk1α and 1 μg of each was digested with Kpn1 and Sal1 and applied to a 0.8% agarose/TAE gel. Lanes 1–5 contain DNA molecular weight markers (Lane 1), Av3nBg and Av3sphk1α digested with Kpn1 (Lanes 2 and 3, respectively) and Av3nBg and Av3sphk1a digested with Sal1 (Lanes 4 and 5, respectively). The DNA fragments were transferred to a nylon membrane and prehybridized in 0.5M NaPO$_4$, 1 mM EDTA, 0.5% BSA, 7% SDS at 65° C. for 2 hours. The membrane was hybridized at 65° C. overnight with the 1531 bp Hind III/Not1-digested fragment used for cloning into the shuttle plasmid and washed in SSC/SDS containing buffers at 65° C. following standard protocols. The membrane was exposed to film for 20 minutes at room temperature. The expected fragment derived from Av3sphk1α was detected by Southern Blot analysis (Data not shown).

Example 2
Sphingosine Kinase Activity

The sphingosine kinase adenoviral vector was characterized first in vitro. Because immunological reagents currently are unavailable for this protein the ability of Av3sphk1α transduced cells to convert sphingosine to SPP was examined.

S8 cells, A549 cells (ATCC No. CCL-185), coronary artery smooth muscle cells (CASMC), or human umbilical vein endothelial cells (HUVEC), were transduced with Av3sphk1α or AV3Null at a multiplicity of infection (MOI) of 100, or were mock transduced.

2 days after transduction, cells were harvested and lysed via freeze-thawing in reaction buffer. Cell lysates were fractionated into cytosol and membrane fractions by centrifugation at 100,000×g for 60 min at 4° C. Sphingosine kinase activity was determined in the presence of 50 µM sphingosine (dissolved in 5% Triton X-100), and [P] $^{32}$ATP containing $MgCl_2$ (200 mM) and incubated for 15 min at 37° C.

Reactions were terminated by addition of 20 µl of 1N HCL, 0.8 ml of chloroform/methanol/HCL (100:200:1, v/v), and 240 µl of chloroform and 240 µl of 2M KCL. Phases were separated by centrifugation. The labeled SPP in the organic phases was separated by thin layer chromatography on silica gel G60 with 1-butanol/ethanol/acetic acid/water (80:20:10:20 v:v) and visualized by autoradiography.

Mock transduced S8, A549, CASMC and HUVEC contained a very low level of sphingosine kinase enzymatic activity. Transduction of S8, A549, CASMC with an Av3Null vector does not substantially alter the amount of sphingosine kinase activity. By contrast, adenoviral transduction of HUVEC apparently increased endogenous sphingosine kinase activity. Transduction of all cell types with Av3sphk1α resulted in substantially higher enzymatic activity. The data indicate that the adenoviral vector encoding sphingosine kinase specifically increases the ability of cells to generate higher levels of SPP. These results indicate the vector expresses a functional sphingosine kinase enzyme that is capable of increasing cellular levels of SPP.

Example 3
In vivo Analysis Using Matrigel Implant Assay

Samples including liquid Matrigel (a sterile extract of basement membrane proteins), admixed with test substances, are prepared beforehand and preloaded into 1.0 ml tuberulin syringes with G27 needles. Animals were anesthetized and 0.5 mls of the undiluted MatriGel containing 250 ng/ml or 1.2 ug per ml of FGF, adenoviral vectors or cells that are transduced with adenoviral vectors were injected subcutaneously into the caudal portion of the midline (1 injection/animal) using a G27 needle. The Matrigel will form rapidly a solid gel that persists for over 7 days. On Day 7, all animals are euthanized by $CO_2$ and Matrigel plugs are harvested for histological analysis and hemoglobin measurement. The tissues are stained for the endothelial cell specific marker, CD31 and for the smooth muscle cell marker, α smooth muscle actin.

Figure 4:
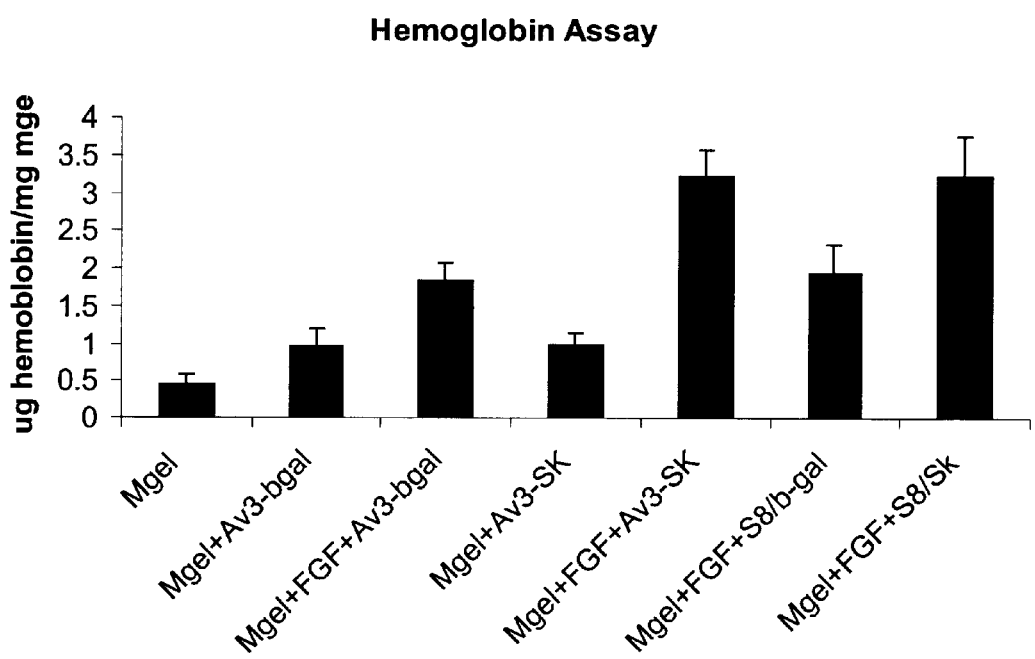
FIG. 4. Hemoglobin assay. Matrigel is snap-frozen with dry ice and dried overnight. The dry weight is recorded and the plug is rehydrated with 0.5 ml of 0.5% Tween and water. After homogenization, the plug is centrifuged at 14,000 rpm for 30 minutes. The supernatant is collected and its absorbance is read at 405 nm and converted to $\mu$g hemoglobin per mg Matrigel using a standard curve generated with hemoglobin standards.

To determine if Av3sphk1α induces angiogenesis in vivo, a matrigel implant model in athymic mice was used (Passaniti, et al, *Lab. Invest.*, Vol. 67, No. 4, pgs. 519–528, 1992) S8 cells transduced with Av3sphk1α at 100 particles per cell are mixed with 0.5 Matrigel and implanted subcutaneously for 7 days. Av3sphk1α clearly enhances bFGF-induced angiogenesis as demonstrated by histological analysis (Data not shown). Appearance of larger, mature vessels as well as increased number of CD-31 positive vessel structure are apparent in the presence of Av3sphk1α transduced cells. By contrast, the control Av3null vector does not enhance angiogenesis. Next, whether direct incorporation of the Av3sphk1α vector into Matrigel is able to augment bFGF induced angiogenesis was examined. 1×10$^9$ total particles was mixed with 250 ng/ml bFGF and tested in the implant assay. As shown in FIG. 4, direct vector incorporation facilitated increased angiogenic response as measured by an increase in the hemoglobin concentration in the Matrigel. The increased angiogenic response is similar to that produced by Av3sphk1α transduced cells. We conclude that overexpression of sphingosine kinase via an adenoviral vector can enhance blood vessel formation substantially in vivo and most strikingly, facilitated an increase in the size and maturity of the new vessels.

Figure 5:
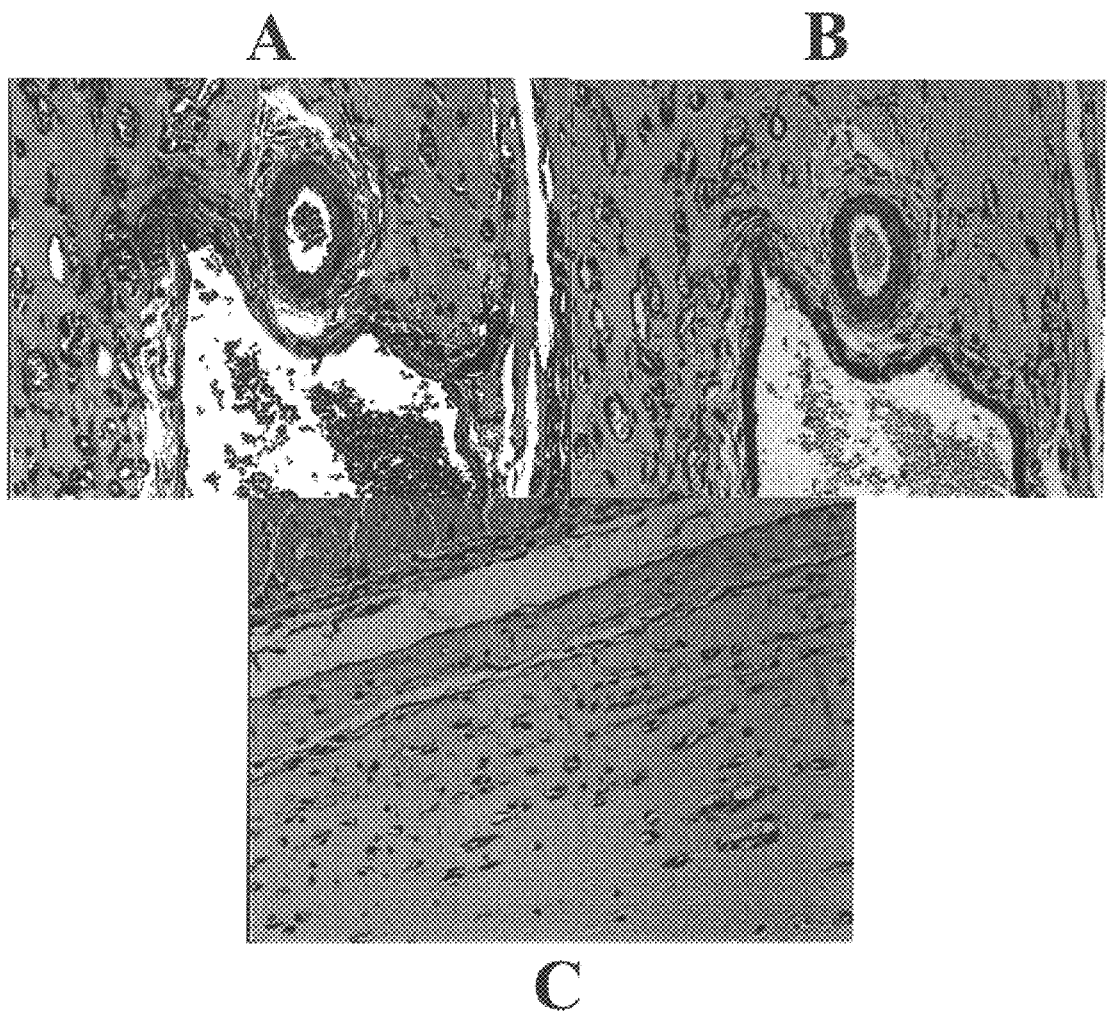
FIG. 5 illustrates the remarkable difference that the addition of an adenoviral vector expressing sphingosine kinase makes in the nature of neovessels formed in an in vivo matrigel system.

FIG. 5 illustrates the remarkable differences that the addition of the adenoviral vector expressing sphingosine kinase makes in the nature of the neovessels that are formed in the in vivo matrigel system. As shown in FIG. 5A, which is a hematoxylin and eosin stained section of matrigel treated with S8 cells transduced with the adenoviral vector encoding sphingosine kinase. There clearly is a vascular network including an arteriole and venule running side by side and a network of capillaries. In addition, these clearly are patent vessels as indicated by the presence of red blood cells, within these vessels. FIG. 5B is the same section stained with α-smooth muscle (α-SM) actin. This section shows the presence of at least a single layer of actin positive cells surrounding the endothelium. By contrast, as shown in FIG. 5C, a matrigel plug treated with FGF generated capillaries but there is a minimal amount of actin positive cells. Greater and more consistent α-SM actin staining in matrigel sections treated with the sphingosine kinase vector or cells transduced with this vector were observed routinely. The FGF-induced vessel had variable amounts of α-SM actin positive cells.

Example 4
Sphingosine Kinase-mediated Protection of Cardiomyocytes

Cell Lines and Culture Conditions: Human fetal cardiomyocytes (Clonetics Corporation, passages 4–7) were grown in 75 cm2 tissue culture flasks (Falcon Primaria) in Smooth Muscle Growth Media-2 (Clonetics Corporation) supplemented with 5% fetal bovine serum, 0.5 µg/ml human recombinant epidermal growth factor, 5 mg/ml insulin, 1 µg/ml human recombinant fibroblast growth factor, and 50 mg/ml gentamicin and 50 µg/ml amphotericin-B at 37° C. in a 95% air/5% CO2 humidified atmosphere. Cells were subcultured by aspiration of the growth medium followed by a 30-sec rinse with a solution of 0.5 mM EDTA/0.25 mg/ml trypsin.

Apoptosis assays: Ischemia in cardiac myocyte cultures was induced by adding serum- and glucose-free Dulbecco's Modified Eagle Medium (Life Technologies) and incubating the cells in an incubator perfused with 95% $N_2$/5% $CO_2$. After the indicated time periods, the cells were removed from the hypoxic incubator, reoxygenated with complete growth medium containing glucose and serum and placed at 37° C. in a 95% air/5%$CO_2$ humidified atmosphere. Cardiac myocytes were heat shocked by immersion into a temperature-controlled water bath (Precision Scientific, Chicago, Ill.) at 42° C. for 30 min. Following exposure to heat shock, the cells were incubated at 37° C. in a $CO_2$ incubator for 6 hr and then analyzed for apoptosis induction. Cells were treated with 10 µM C6-ceramide (N-Hexanoylsphingosine) overnight (Biomol Research Laboratories, Plymouth Meeting, Pa.) in serum-free medium prior to assessment for apoptosis. Cardiac myocytes were examined for morphological features of apoptosis (chromatin condensation and fragmentation) by fluorescence microscopy using acridine orange and ethidium bromide as described previously (Hreniuk, D., Garay, M, Gaarde, W., Monia, B. P., McKay, R. A. and Cioffi, C. L. Mol Pharmacol. 59: 867–874, 2001). Briefly, apoptosis was assessed by the addition of 50 µl of a 1:1 stock solution of ethidium bromide/acridine orange (Sigma) to 1 ml of culture media on the cells growing in 35 cm culture dishes. A coverslip was attached and the morphological features of apoptosis were monitored by fluorescence microscopy using a microscope equipped with FITC filter at 600×. At least 200 cells from randomly selected fields were counted and quantitated according to the following formula: % apoptotic cells=number of apoptotic cells/total number of cells counted×100.

Adenovirus Transduction of Cardiac Myocytes: Transduction of human cardiac myocytes with adenoviral vectors was optimized with the adenoviral vector encoding the marker gene nuclear βgalactosidase (Av3ng). Briefly, cardiac myocytes, grown in 35 mm Primaria tissue culture dishes, were infected with adenoviral vectors at 10–500 particles per cell in 0.5 ml serum-free medium in the presence of a 1:1000 μl dilution of Fugene-6 for six hours at 37° C., and then 1 ml complete growth medium was added for overnight incubation. Cardiac myocytes grown in 96-well Primaria culture plates were infected with Av3nBg in 100 μl serum-free medium for six hours at 37° C. and then 100 μl of complete growth medium was added for overnight incubation.

Figure 6:
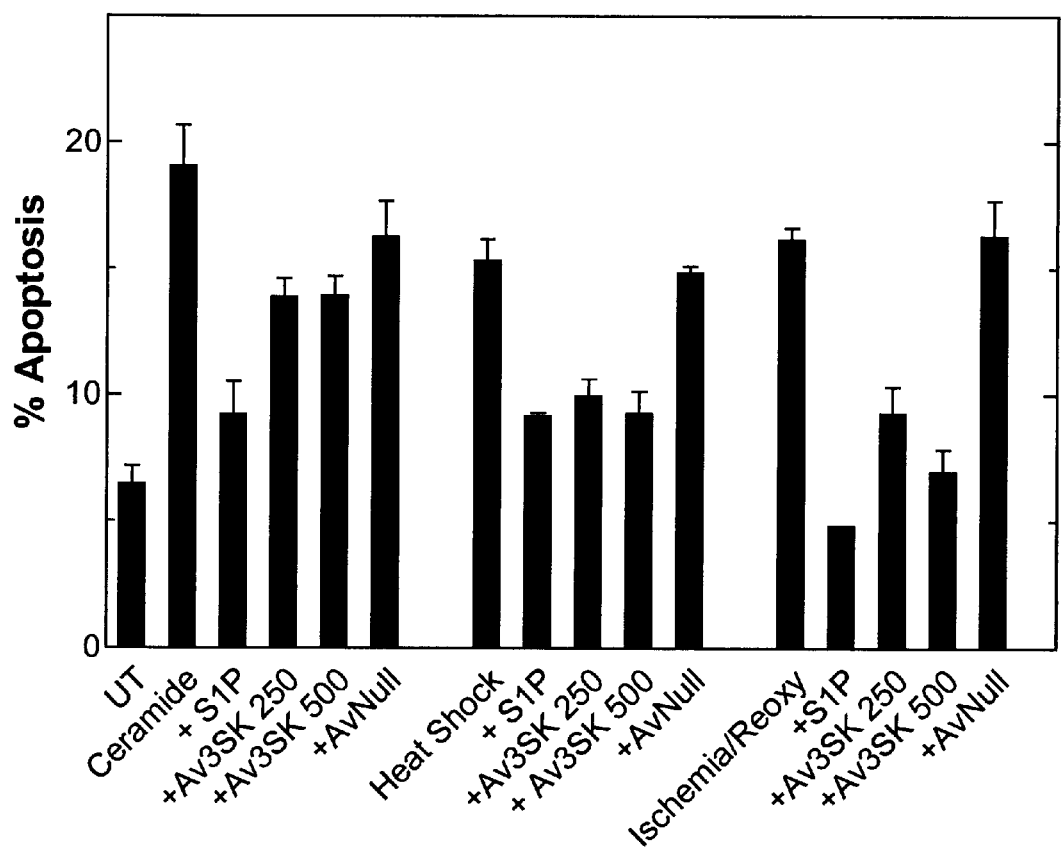
FIG. 6 illustrates the sphingosine kinase mediated protection of cardiomyocytes.

Overexpression of Sphingosine Kinase protects cardiomyocytes from apoptosis: The AV3SK vector and its enzymatic product, sphingosine 1-phosphate (S-1-P) were both evaluated for possible inhibition of apoptosis in human cardiac myocytes induced by ceramide (n=3), heat shock (n=3), ischemia/reoxygenation (n=2). For vector-mediated studies, experiments were performed 3 days after vector treatment. The data, shown in FIG. 6, indicate that S-1-P is a potent inhibitor of human cardiac myocyte cell death. Av3SK transduced cells are also almost completely resistant to heat shock and ischemia/reoxygenation-induced apoptosis (FIG. 6). However, Av3SK vectors can only partially inhibit ceramide-induced apoptosis. This data in cardiac myocytes supports a cardioprotective role for sphingosine kinase and S1P. The use of a gene therapy vector to express sphingosine kinase represents a treatment modality for the long-term protection of cardiac myocytes from injury and protect against congestive heart failure.

The disclosure of all patents, patent applications, publications (including published patent applications), depository accession numbers, and database accession numbers are incorporated herein, by reference, in their entirety to the same extent as if each individual patent, patent application, publication, depository accession number, and database accession number were specifically and individually incorporated by reference.

It is to be understood, however, that the scope of the present invention is not to be limited to the specific embodiments described above. The invention may be practiced other than as particularly described and still be within the scope of the accompanying claims.

What is claimed is:

1. An adenoviral vector comprising a polynucleotide encoding a sphingosine kinase and a polynucleotide encoding an additional angiogenic protein selected from the group consisting of: VEGF, FGF, IGF, an angiopoietin, PD-EGF, TGF-β, HIF1-α, nitric oxide synthase, MCP-1, Interleukin-8, and an ephrin.

2. The adenoviral vector according to claim 1, wherein said additional angiogenic protein is VEGF.

3. The adenoviral vector according to claim 1, wherein said additional angiogenic protein is FGF.

4. The adenoviral vector according to claim 1, wherein sail additional angiogenic protein is IGF.

5. The adenoviral vector according to claim 1, wherein said additional angiogenic protein is an angiopoietin.

6. The adenoviral vector according to claim 1, wherein said additional angiogenic protein is PD-EGF.

7. The adenoviral vector according to claim 1, wherein said additional angiogenic protein is TGF-β.

8. The adenoviral vector according to claim 1, wherein said additional angiogenic protein is HIF1-α.

9. The adenoviral vector according to claim 1, wherein said additional angiogenic protein is nitric oxide synthase.

10. The adenoviral vector according to claim 1, wherein said additional angiogenic protein is MCP-1.

11. The adenoviral vector according to claim 1, wherein said additional angiogenic protein is Interleukin-8.

12. The adenoviral vector according to claim 1, wherein said additional angiogenic protein is an ephrin.

* * * * *